(12) United States Patent
    Cannon

(10) Patent No.: US 9,889,016 B2
(45) Date of Patent: Feb. 13, 2018

(54) ADJUSTABLE TOTAL DISC REPLACEMENT DEVICE

(71) Applicant: Ben Cannon, Glendale, AZ (US)

(72) Inventor: Ben Cannon, Glendale, AZ (US)

(*) Notice: Subject to any disclaimer, the term of this patent is extended or adjusted under 35 U.S.C. 154(b) by 0 days.

(21) Appl. No.: 14/959,951

(22) Filed: Dec. 4, 2015

(65) Prior Publication Data

US 2016/0158025 A1    Jun. 9, 2016

Related U.S. Application Data

(60) Provisional application No. 62/087,612, filed on Dec. 4, 2014.

(51) Int. Cl.
    *A61F 2/44*     (2006.01)
    *A61F 2/30*     (2006.01)
    *A61F 2/46*     (2006.01)

(52) U.S. Cl.
    CPC .... *A61F 2/4425* (2013.01); *A61F 2002/3037* (2013.01); *A61F 2002/30224* (2013.01); *A61F 2002/30405* (2013.01); *A61F 2002/30553* (2013.01); *A61F 2002/30565* (2013.01); *A61F 2002/30578* (2013.01); *A61F 2002/30649* (2013.01); *A61F 2002/469* (2013.01); *A61F 2002/4698* (2013.01); *A61F 2250/0004* (2013.01)

(58) Field of Classification Search
    CPC .......... A61F 2/4425; A61F 2002/30224; A61F 2002/3037; A61F 2002/30405; A61F 2002/30553; A61F 2002/30565; A61F 2002/30578; A61F 2002/30649; A61F 2002/469; A61F 2002/4698; A61F 2250/0004
    USPC ......... 623/17.13, 17.14, 17.15, 17.16, 23.47; 606/279
    See application file for complete search history.

(56) References Cited

U.S. PATENT DOCUMENTS 7,531,002 B2 * 5/2009 Sutton ..................... A61F 2/442
                                                    606/90
2004/0153160 A1 * 8/2004 Carrasco ............... A61F 2/4611
                                                    623/17.15

(Continued)

*Primary Examiner* — Pedro Philogene
*Assistant Examiner* — David C Comstock
(74) *Attorney, Agent, or Firm* — Schmeiser, Olsen & Watts LLP

(57) ABSTRACT

Disclosed is an implantable artificial intervertebral disc joint replacement device for implantation between adjacent vertebral bodies. The device allows selective positioning of a disc implant element and comprises translatable surfaces, a mechanism for translation, a means for bone attachment, and an integrated disc implant. The device can be used in the lumbar, thoracic, and cervical regions of the spine in single or multi-level configurations. When implanted in a patient, the device includes an upper (cranial) component and a lower (caudal) component attached to the vertebral body above and below the replaced intervertebral disc respectively, with the joint implant integrated into the translatable surfaces. Following implantation, precise positioning of the joint implant within the intervertebral space with respect to the spinal axis is then adjusted based upon the particular anatomical and functional needs of the individual patient to satisfy spinal range of motion and stability requirements.

19 Claims, 17 Drawing Sheets

(56) References Cited

U.S. PATENT DOCUMENTS

2004/0254644 A1* 12/2004 Taylor .................. A61F 2/4425
                                                            623/17.13
2009/0125111 A1*  5/2009 Copf, Jr. ............... A61F 2/4425
                                                            623/17.16
2009/0192618 A1*  7/2009 Zielinski .............. A61F 2/4425
                                                            623/17.16

* cited by examiner

ADJUSTABLE TOTAL DISC REPLACEMENT DEVICE

CROSS REFERENCE TO RELATED APPLICATION

This application claims priority from U.S. Patent Application No. 62/087,612, filed Dec. 4, 2014 and entitled "Adjustable Total Disc Replacement Device," which is incorporated entirely herein by reference.

BACKGROUND OF THE INVENTION

Technical Field

This invention relates to artificial intervertebral joints. In particular, the invention relates to artificial implantable intervertebral disc joints with controls for adjustable positioning of surfaces related to load-bearing and force-distribution.

State of the Art

The spinal column is a segmental chain of vertebrae. Each vertebra comprises an anterior, roughly cylindrical vertebral body and posterior elements forming bony canal surrounding the spinal cord and spinal nerve roots. The posterior bony canal components of each vertebra articulate with adjoining vertebra above and below at facet joints forming a load-bearing structure known as the posterior column. The anterior vertebral bodies, in turn, articulate at intervertebral disc joints collectively forming the load-bearing structure known as the anterior column. In humans and other animals, axial loads are distributed between the anterior and posterior columns. Motion at the facet joints affects load distribution forces in both columns and, similarly, motion at the intervertebral disc joints also affects load distribution forces in both columns.

The human intervertebral disc ("IVD") is a soft-tissue structure sandwiched between the bony end-plates of the vertebral body above (cranial) and the vertebral body below (caudal). This soft-tissue disc comprises a fibrous ring-shaped wall of tissue (anulusus fibrosis) surrounding a gelatinous core (nucleus pulposis.) The natural IVD space allow for motion in the anterior-posterior plane, such as flexion and extension; lateral motion to either side, and axial rotation. The human IVD joint has a non-fixed, mobile center of rotation ("COR"), or collection of multiple CORs otherwise known as a centrode, about which axial rotation occurs.

The IVD joint is vulnerable to a variety of degenerative processes, of both traumatic and non-traumatic etiologies, which are sometimes treated by surgically replacing the IVD joint with a prosthetic device. Available prosthetic devices, however, are limited in capacity to reproduce the natural load-bearing mechanics and range of motion of the native IVD joint.

Accordingly, what is needed is a device that provides a structure and mechanism of reproducing a more natural range of motion of an IVD joint.

DISCLOSURE OF EMBODIMENTS OF THE INVENTION

The foregoing and other features and advantages of the invention will be apparent to those of ordinary skill in the art from the following more particular description of the invention and the accompanying drawings.

Disclosed is an embodiment of a total intervertebral disc replacement device comprising a cranial member, further comprising a cranial base body; a cranial adjustable body coupled to the cranial base body, wherein the cranial adjustable body adjusts along a cranial AP axis with respect to the cranial base body; a cranial articular surface coupled to the cranial adjustable body; a caudal member, further comprising a caudal base body; a caudal adjustable body coupled to the caudal base body, wherein the caudal adjustable body adjusts along a caudal AP axis with respect to the caudal base body and wherein the caudal AP axis is parallel to the cranial AP axis; a caudal articular surface coupled to the caudal adjustable body; and a joint comprising the cranial articular surface and the caudal articular surface, wherein the caudal articular surface moveably engages with the cranial articular surface.

In some embodiments, the cranial adjustable body is slidably coupled to the cranial base body and the caudal adjustable body is slidably coupled to the caudal base body In some embodiments, the total intervertebral disc replacement device further comprises an attachment apparatus, wherein the cranial base body is coupled to a cranial vertebral body and the caudal base body is coupled to a caudal vertebral body by the attachment apparatus. In some embodiments, the attachment apparatus comprises a biocompatible adhesive coupled to a cranial adhesive surface of the cranial base body and to a caudal adhesive surface of the caudal base body. In some embodiments, the attachment apparatus comprises a cranial screw strut; a cranial bone screw; a caudal screw strut; and a caudal bone screw.

In some embodiments, the cranial articular surface comprises a concave curvature and the caudal articular surface comprises a convex curvature, wherein the convex curvature corresponds to the concave curvature.

In some embodiments, the total intervertebral disc replacement device further comprises a first cranial actuator coupled to the cranial base body and engaging the cranial adjustable body; and a first caudal actuator coupled to the caudal base body and engaging the caudal adjustable body. In some embodiments, the first cranial actuator limits motion of the cranial adjustable body relative to the cranial base body along the cranial AP axis, and the first caudal actuator limits motion of the caudal adjustable body relative to the caudal base body along the caudal AP axis. In some embodiments, the first cranial actuator adjusts the position of the cranial adjustable body relative to the cranial base body along the cranial AP axis, and the first caudal actuator adjusts the position of the caudal adjustable body relative to the caudal base body along the caudal AP axis. In some embodiments, further comprises a unitary actuator coupled to the cranial base body or the caudal base body, and engaging the cranial adjustable body or the caudal adjustable body, wherein activation of the unitary actuator positions the joint relative the cranial base body and the caudal base body.

In some embodiments, the total intervertebral disc replacement device further comprises a first cranial track wherein a long axis of the cranial track is parallel to the cranial AP axis; a first cranial biasing member engaging the cranial adjustable body, wherein the first cranial biasing member biases motion of the cranial adjustable body in a direction along the cranial AP axis relative to the cranial base body; a first caudal track wherein a long axis of the caudal track is parallel to the caudal AP axis; and a first caudal biasing member engaging the caudal adjustable body, wherein the first caudal biasing member biases motion of the caudal adjustable body in a direction along the caudal AP axis relative to the caudal base body.

Disclosed is a total intervertebral disc replacement device comprising a cranial member, further comprising a cranial base body; a cranial adjustable body slidably coupled to the cranial base body, wherein the cranial adjustable body slides within a cranial plane with respect to the cranial base body; a cranial articular surface coupled to the cranial adjustable body; a caudal member, further comprising a caudal base body; a caudal adjustable body slideably coupled to the caudal base body, wherein the caudal adjustable body slides within a caudal plane with respect to the caudal base body and wherein the caudal plane is parallel to the cranial plane; and a caudal articular surface coupled to the caudal adjustable body, wherein the caudal articular surface moveably engages with the cranial articular surface.

In some embodiments, the total intervertebral disc replacement device further comprises a first cranial actuator coupled to the cranial base body and engaging the cranial adjustable body, wherein the first cranial actuator limits sliding motion of the cranial adjustable body with respect to the cranial base body along a cranial AP axis; a second cranial actuator coupled to the cranial base body and engaging the cranial adjustable body, wherein the second cranial actuator limits sliding motion of the cranial adjustable body with respect to the cranial base body along a cranial lateral axis; a first caudal actuator coupled to the caudal base body and engaging the caudal adjustable body, wherein activation of the first caudal actuator limits sliding motion of the caudal adjustable body with respect to the caudal base body along a caudal AP axis; and a second caudal actuator coupled to the caudal base body and engaging the caudal adjustable body, wherein the second caudal actuator limits sliding motion of the caudal adjustable body with respect to the caudal base body along a caudal lateral axis.

In some embodiments, the total intervertebral disc replacement device further comprises an AP movement mechanism comprising a first cranial track wherein a long axis of the cranial track is parallel to the cranial AP axis; a first cranial biasing member engaging the cranial adjustable body, wherein the cranial biasing member biases motion of the cranial adjustable body in a direction along the cranial AP axis relative to the cranial base body; a first caudal track wherein a long axis of the caudal track is parallel to the caudal AP axis; and a first caudal biasing member engaging the caudal adjustable body, wherein the first caudal biasing member biases motion of the caudal adjustable body in a direction along the caudal AP axis relative to the caudal base body; and a lateral movement mechanism comprising a second cranial track wherein a long axis of the second cranial track is parallel to a cranial lateral axis; a second cranial biasing member engaging the cranial adjustable body, wherein the second cranial biasing member biases motion of the cranial adjustable body in a direction along the cranial lateral axis relative to the cranial base body; and a second caudal track wherein a long axis of the second caudal track is parallel to a caudal lateral axis; and a second caudal biasing member engaging the caudal adjustable body, wherein the second caudal biasing member biases motion of the caudal adjustable body in a direction along the caudal lateral axis relative to the caudal base body.

Disclosed is a method of surgically implanting a total intervertebral disc replacement device, comprising the steps of excising an intervertebral disc joint; coupling an intervertebral total disc replacement device to a vertebral body; and articulating a cranial articular surface with a caudal articular surface of a total intervertebral disc replacement device.

In some embodiments, the method further comprises a step radiographing the position of the total intervertebral disc replacement device. In some embodiments, the method further comprises a step intraoperatively fluoroscoping the position of the total intervertebral disc replacement device. In some embodiments, the method further comprises a step adjusting the position of an articular surface of the coupled total intervertebral disc replacement device.

DETAILED DESCRIPTION OF EMBODIMENTS OF THE INVENTION

Figure 1A:
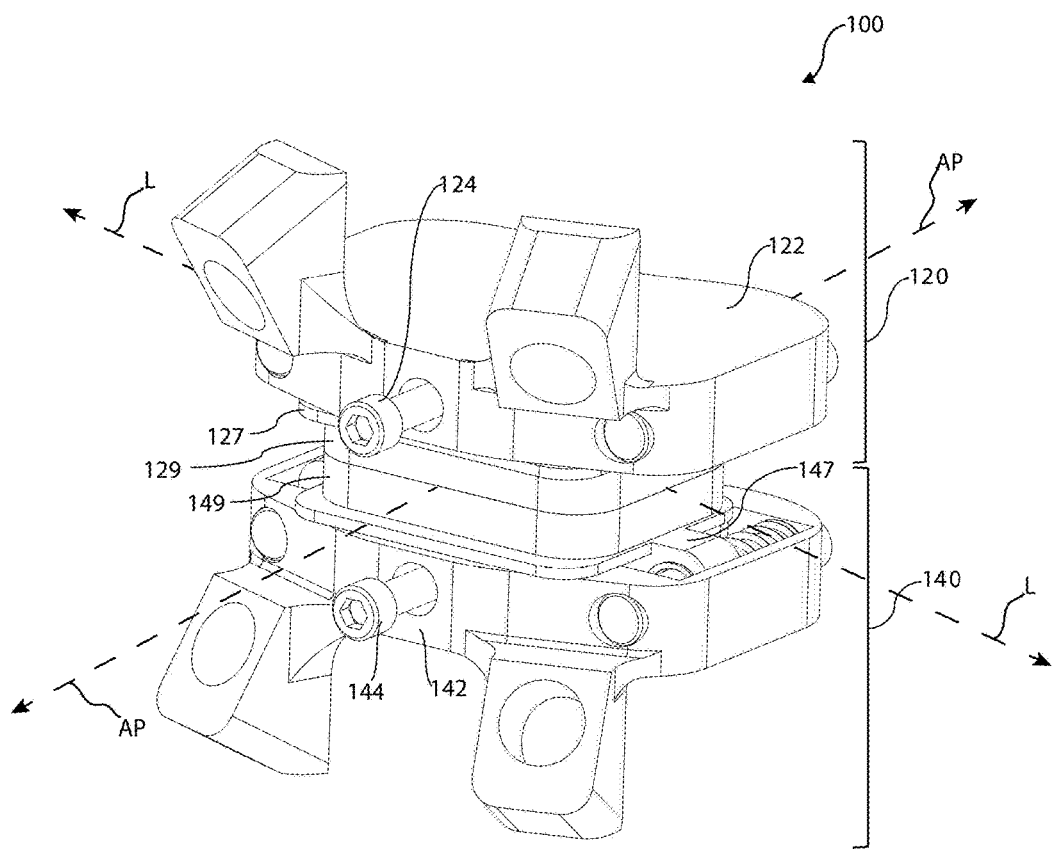
FIG. 1(A) is a perspective view of a total intervertebral disc replacement device.

As discussed above, the disclosed invention relates to artificial IVD joints. In particular, the invention relates to artificial implantable IVD joints with a "floating" COR, including artificial IVD joints with controls for adjusting the COR position.

Total disc replacement ("TDR") devices are available for treatment of patients with a wide variety of severe inflammatory and degenerative conditions of the cervical IVD, including but not limited to spondylolisthesis, degenerative disc disease, spinal cord nerve compression, and trauma. Motion-preserving TDR procedures for cervical IVD are available for patients. The spine surgeon may choose and favor a TDR implant device based on the patient's anticipated postoperative activity level and to minimize adjacent segment disease ("ASD"). Commonly employed TDR implant devices use a ball-and-socket or similar design with a fixed COR and rotation-coupled translation. With constrained motion about a fixed COR, the positioning of the TDR implant device intraoperatively may, therefore, affect resulting postoperative kinematics.

In vivo, the intervertebral axis of rotation is affected by physiologic conditions. With reference to mechanics, the instantaneous COR of a rigid plane moving within a plane is a centrode. Fixed-position TDR devices are typically implanted intraoperatively by centering the TDR endplates in the midline of the vertebral bodies, creating a fixed COR. The patient's natural COR, however, is not fixed, but changes with spinal motion. The axis of rotation of two vertebral bodies separated by an IVD is dynamic, describing a centrode. This dynamic axis of rotation, however, is not duplicated by currently available TDR devices. In current TDR devices, the axis of rotation is fixed and translation is allowed only when coupled with rotation.

Ideally, vertebral endplate positioning of a TDR device should not necessarily be centered over the COR of the vertebral bodies, which is not fixed, but rather be determined based upon the biomechanical consequences of anterior-posterior ("A/P") and lateral variations of the vertebral endplate positioning of the TDR device. The biomechanics may be defined and consequences of various TDR endplate positions predicted by measuring changes in facet loading and the instantaneous axis of rotation ("IAR") with flexion and extension, lateral bending, and rotation at various levels following TDR. One way to obtain these measurements is by performing TDR in fresh human cadaver spines and then taking the measurements directly in various states of A/P flexion/extension, lateral bending, and axial rotation.

Because of the fixed nature of currently available TDR devices, the endplate placement position on the vertebral body affects the IAR, the overall range of motion ("ROM"), the facet joint load distribution, and vertebral coupling—combination of lateral bending with axial rotation depending upon the anatomic characteristics of the intervertebral and facet joints at a given level of the spine. To replicate the moving non-fixed nature of the COR in the centrode, a biasing member may be used, a non-limiting example being a spring, to control the travel of an adjustable body coupled to an articular surface. For example, a stiff spring would allow less movement of the adjustable body (small centrode envelope) compared to a relatively less-stiff spring (large centrode envelope).

Embodiments of the invention address this and other limitations by providing a TDR device which allows for adjusting the COR by partially replicating the natural "floating" COR. A total IVD replacement device may be adjusted based upon force distribution across the intervertebral and facet joint surfaces during rotation and IAR characteristics with flexion/extension, lateral bending, and axial rotation. Adjustable positioning allows the spine surgeon to optimize load distribution and stability, providing optimal performance based upon the physical parameters, age, and activity requirements of the individual patient. Embodiments of the invention selectively position prosthetic IVD joint articular surfaces between opposing vertebral end plates to account for the non-fixed nature of the COR, or centrode, of the natural IVD joint.

FIG. 1(A) shows an total IVD replacement total IVD replacement device 100. Total IVD replacement device 100, in some embodiments, is surgically implanted in the operating room under general anesthesia to replace a diseased or damaged IVD. FIG. 1(C) and FIG. 1(D) show a front perspective and front view respectively of an example embodiment of total IVD replacement device 100 implanted between the fifth cervical vertebra and the sixth cervical vertebra of a human cervical spine. The various embodiments of total IVD replacement device 100 may be sized and otherwise configured appropriately for implantation at cervical spinal levels in some embodiments, at thoracic spinal levels in some embodiments, and at lumbar spinal levels in some embodiment. In some embodiments, implantation requires substantial removal of the IVD, including some or all of the annulus and some or all of the nucleus pulposis. In some embodiments, a portion of the vertebral body above and below the disc space is also removed as necessary to create a space for insertion of total IVD replacement device 100 without substantially altering the length of and/or transmitting a compressing or distracting force to other levels of the spinal column. This may be somewhat appreciated by the embodiment shown in FIG. 1(D). An anterior surgical approach for implantation of total IVD replacement device 100 is preferable, in some embodiments. In some embodiments, a lateral surgical approach may be used to expose the adjoining vertebral bodies for IVD replacement. In some embodiments, still other surgical approaches may be used.

Figure 1B:
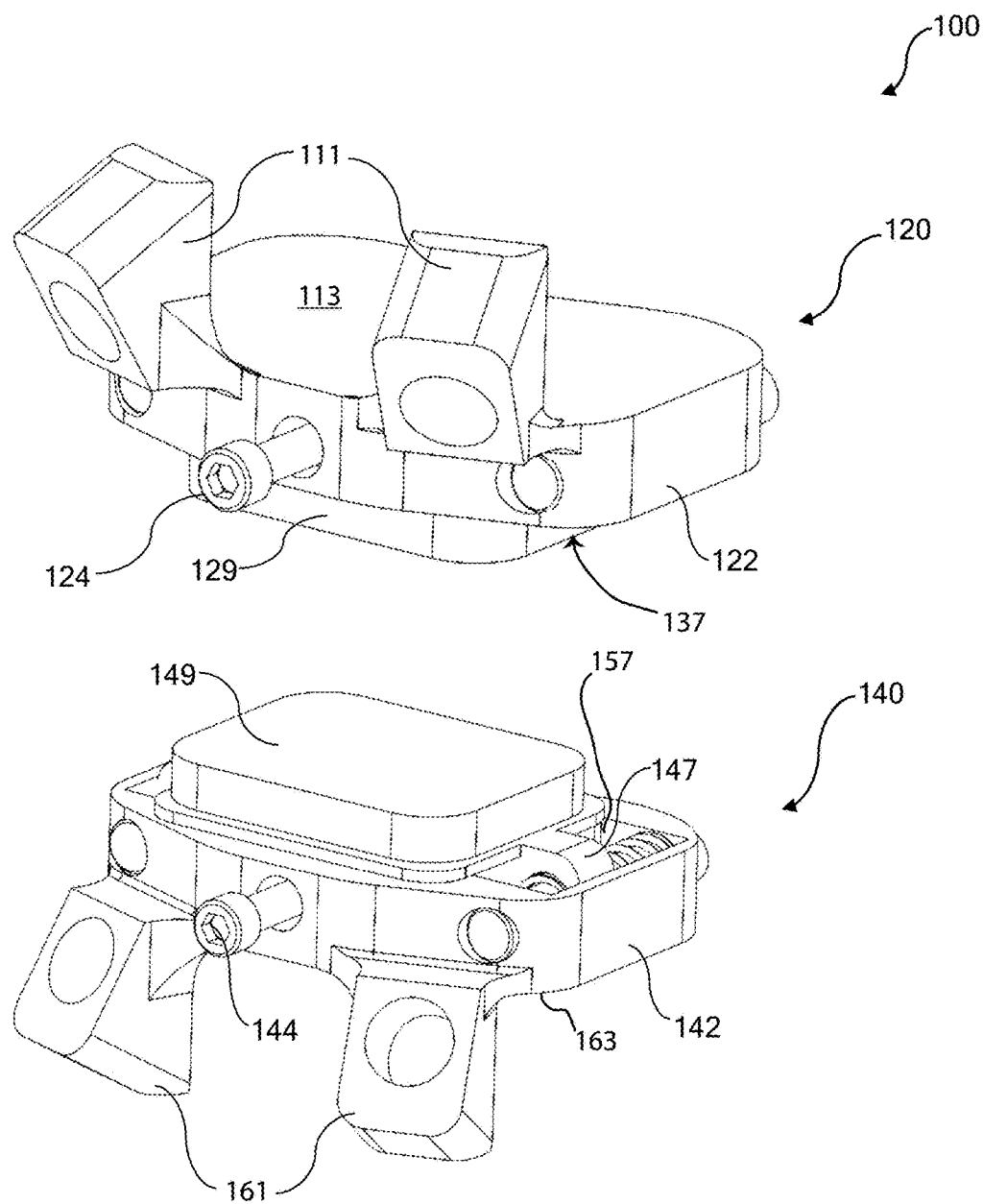
FIG. 1(B) is a perspective view of a cranial member and a caudal member of a total intervertebral disc replacement device.
Figure 1C:
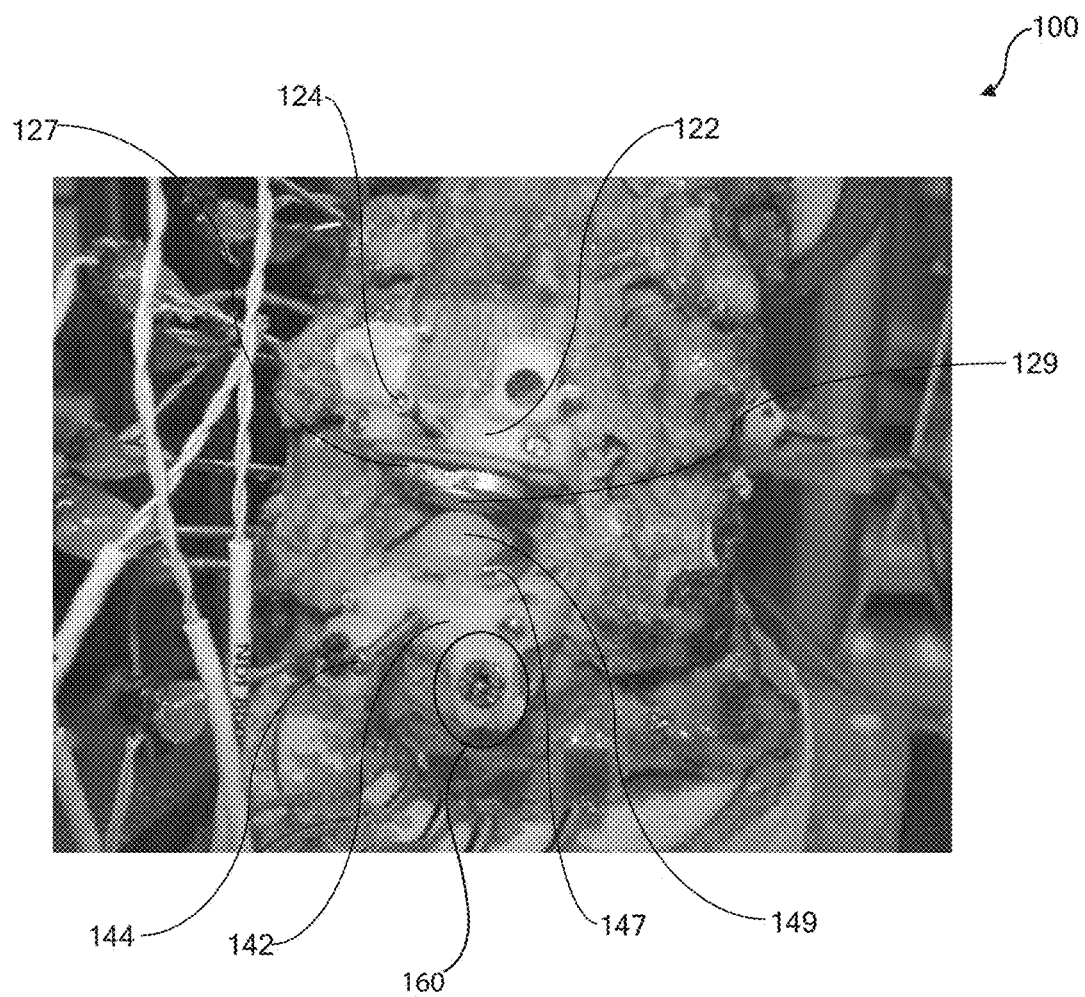
FIG. 1(C) is a perspective view of a total intervertebral disc replacement device implanted in a cervical spine, with a cranial articular surface and a caudal articular surface partially separated.
Figure 1D:
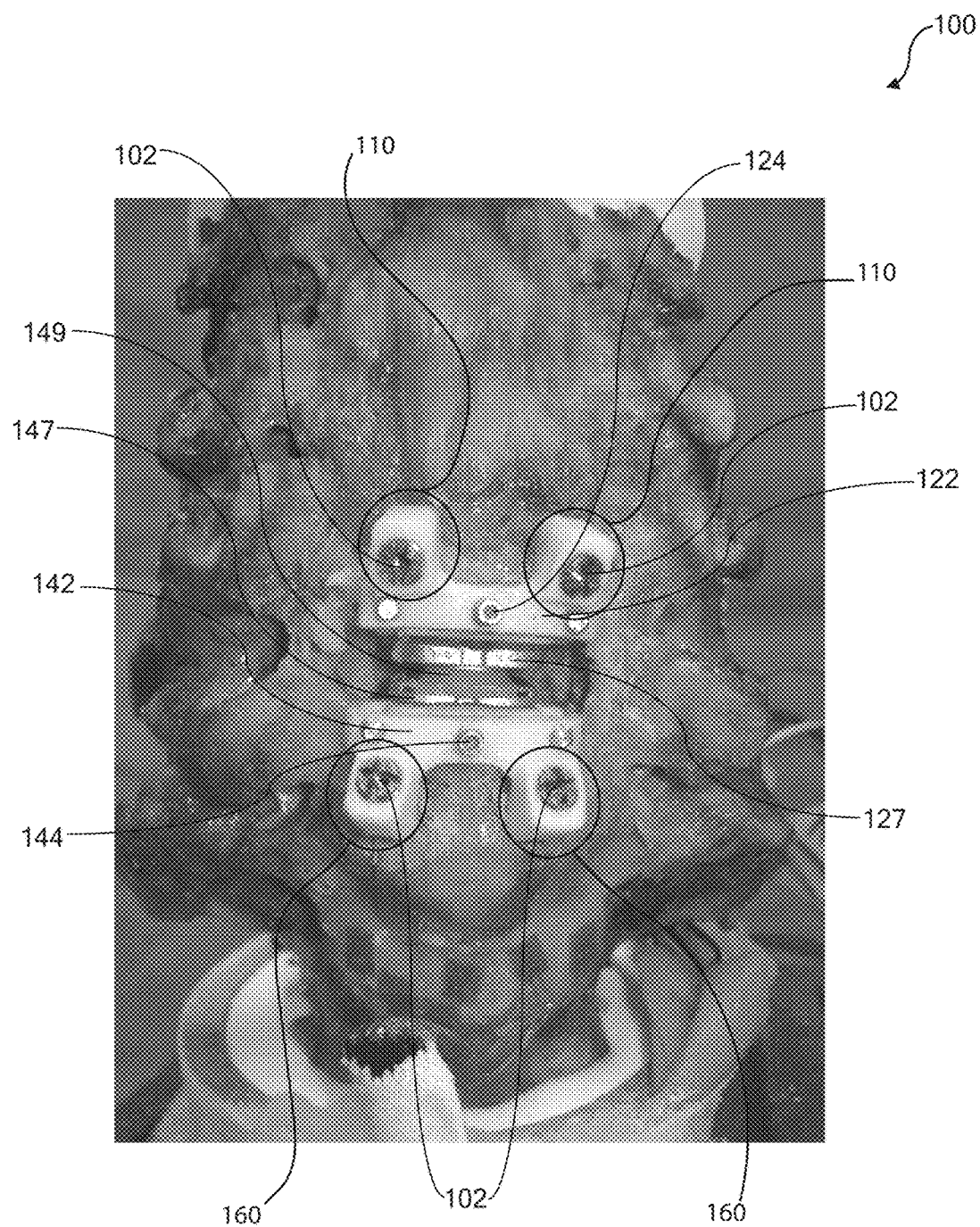
FIG. 1(D) is a front view of a total intervertebral disc replacement device implanted in a cervical spine, with cranial articular surface 129 contacting caudal articular surface 149.

As shown in the embodiment illustrated in FIG. 1(A) and FIG. 1(B), total IVD replacement device 100 comprises two primary components: a cranial member 120 and a caudal member 140. Cranial member 120 and caudal member 140 are each an assembly of components (see exploded views in FIG. 8-FIG. 10.) In the example embodiment shown in the drawing figures, and in some other embodiments, cranial member 120 and caudal member 140 are the same, wherein caudal member 140 is merely an upside-down cranial member 120. In no way, however, is this intended to be limiting. Some embodiments of the invention employ, for example, different shapes, articular surfaces, actuator means, adjustable body-base body coupling means, and other aspects distinguishing cranial member 120 and caudal member 140 from one another.

Cranial member 120 and caudal member 140 each, in some embodiments, comprise a base body and an adjustable body coupled to an articular surface, wherein the adjustable body is moveable in relation to the base body. In some embodiments, the adjustable body is moveable along an anteroposterior axis AP, as shown in FIG. 1(A). In some embodiments, the adjustable body is movable along a lateral axis L, as shown in FIG. 1(A). In some embodiments, the adjustable body is movable along both anteroposterior axis AP and lateral axis L. In some embodiments, the adjustable body position is controlled by a biasing member acting along anteroposterior axis AP. In some embodiments, the adjustable body is controlled by a biasing member acting along lateral axis L. In some embodiments, the adjustable body is positioned by an actuator, wherein a spine surgeon or other healthcare provider may adjust the position of the adjustable body with respect to its respective base body. These example embodiments are discussed in detail herein below.

FIG. 1 also shows a cranial base body 122 that, when implanted in a patient, attaches to the caudal aspect of the vertebral body immediately cranial to the IVD replacement level. For example, in an IVD replacement at C5-C6, cranial base body 122 attaches to the caudal aspect of the fifth cervical vertebral body. Also in this example, and as suggested by FIG. 1(D), a caudal base body 142 attaches to the cranial aspect of the sixth cervical vertebral body.

Cranial base body 122, caudal base body 142, and other components of total IVD replacement device 100 are constructed from non-toxic, biocompatible substances, such as those known in the art and currently used in other prosthetic devices. Examples include polyethylene for articular surfaces. Cobalt-chromium alloys, titanium, titanium allows, tantalum, zirconium and its alloys, and polyethylene may be used for the base bodies, adjustable bodies, and other components of total IVD replacement device 100. There materials are listed by way of example only. Other non-toxic, corrosion-resistant, biocompatible materials are be used, in some embodiments.

In some embodiments, a cranial attachment apparatus 110 couples cranial base body 122 to a caudal aspect of a cranial vertebral body and a caudal attachment apparatus couples caudal base body 142 to the cranial aspect of a caudal vertebral body. In some embodiments, such as the embodiment shown in FIG. 1(D), cranial attachment apparatus 110 comprises a cranial screw strut 111 and a cranial bone screw 112. Two cranial bone screws 112 engaging cranial base body 122 through a pair of cranial screw struts 111 and two caudal bone screws 162 engaging caudal base body 142 through a pair of caudal screw struts 161 are shown in the embodiment illustrated in FIG. 1(D). This is not meant to be limiting, other suitable mechanical attachment apparatuses can be employed. Another apparatus attaching a base body to an adjacent vertebral body is a biocompatible bone cement coupled to a cranial adhesive surface 113 or a caudal adhesive surface 163. Examples of bone cement include, but are not limited to, synthetic self-curing compounds such as polymethyl methacrylate ("PMMA") and methyl methacrylate ("MMA.") The mechanical attachment apparatuses may comprise bone screw(s) biocompatible adhesive, or a combination of bone screw(s) 102 and biocompatible adhesive. Other fasteners, cements, or alternative attachment or coupling apparatuses are employed in some embodiments to maintain total IVD replacement device 100 coupled to adjacent vertebral bodies, including natural in-vivo anatomic structures and forces, in some embodiments.

As shown by the various exploded views in the drawing figures referenced above and further discussed below, cranial member 120 and caudal member 140 also comprise an example of a total IVD replacement device 100 wherein the respective adjustable bodies are movably coupled to the respective base bodies, in some embodiments. Cranial member 120 and caudal member 140 each comprise an articular surface; cranial adjustable body 127 of cranial member 120 comprises a cranial articular surface 129 and caudal adjustable body 147 of caudal member 140 comprises a caudal articular surface 149.

Cranial articular surface 129 and caudal articular surface 149 moveably engage one another to form an artificial joint interface of total IVD replacement device 100 and reconstruct the motion, load-bearing, and force distribution characteristics of the replaced IVD. Cranial articular surface 120 and caudal articular surface 140 are shown in FIG. 2-FIG. 10 as flat, planar surfaces. This is not meant to be limiting, but rather to offer a simple example for clarity. Cranial articular surface 129 and caudal articular surface 140 may be fashioned into any manner of complimentary shapes that moveably engage one-another to allow for motion across the total IVD replacement device 100. One example of such complimentary shapes is a partial ball-and-socket configuration, as in the embodiment of total IVD replacement device 100 shown in FIG. 1(C) and FIG. 1(D). These two figures show an embodiment of total IVD replacement device 100 wherein caudal articular surface 149 is a partial convexity, as shown by FIG. 1(C), and cranial articular surface 129 is a corresponding partial concavity (incompletely shown by the figure.) In alternative embodiments, the convexity may be on cranial articular surface 120 and the concavity on caudal articular surface 149. Other shapes and examples are possible for cranial articular surface 120 and caudal articular surface 149. In some embodiments, the artificial joint interface is a surface allowing only flexion-extension.

In the example embodiment shown in FIG. 1(B), caudal articular surface 149 is coupled to a caudal adjustable body 147 of caudal member 140. In the embodiment shown in FIG. 1(A) and FIG. 1(B), caudal base body 147 comprises a second recess 157 defining an inner volume having a perimeter. Second adjustable body 147 is coupled within second recess 157 and moveable within the perimeter of second recess 157. Caudal adjustable body 147 extends from the inner volume of second recess 157. In some embodiments, a first caudal actuator 144 engages caudal adjustable body 147. In some embodiments, a second caudal actuator 145 (not shown) engages caudal adjustable body 147. In the embodiments shown, caudal adjustable body 147 moves parallel to anteroposterior line AP (shown in FIG. 1(A)). In some embodiments (not shown), caudal adjustable body 147 moves parallel to lateral line L, perpendicular to anteroposterior line AP. In some embodiments, caudal adjustable body 147 moves two-dimensionally in a plane wherein anteroposterior line AP and lateral line L are coplanar, defining a plane wherein the instantaneous COR of caudal adjustable body 147 is located within the plane. In some embodiments, first caudal actuator 144 engages caudal adjustable body 147 and controls movement of caudal adjustable body 147 in a direction parallel with anteroposterior line AP. In some embodiments, second caudal actuator 145 engages caudal adjustable body 147 and controls movement of caudal adjustable body 147 in a direction parallel with lateral line L. In some embodiments, caudal adjustable body 147 remains in a non-fixed position, moving in the plane defined by the coplanar lines line AP and line L.

In some embodiments, caudal adjustable body 147 is adjusted to a non-fixed position or partially fixed position with an instantaneous COR located on a plane defined by the A/P axis and the lateral axis. In these and some other embodiments, second actuator activates caudal adjustable body 147 so as to control motion along the A/P axis, the lateral axis, or a combination of both the A/P and the lateral axes.

Similar to caudal member 140, cranial member 120, in some embodiments, comprises a cranial adjustable body 127 comprising a cranial articular surface 129. Cranial base body 122 comprises a first recess 137 defining an inner volume having a perimeter. Cranial adjustable body 127 is coupled within first recess 137 and moveable within the perimeter of first recess 137. Cranial adjustable body 127 extends from the inner volume of first recess 137. In some embodiments, a first cranial actuator 124 engages cranial adjustable body 127. In some embodiments, first cranial actuator 124 or second cranial actuator 125 control movement of cranial adjustable body 127 in scope and manner similar to the activation and control of caudal adjustable body 147 by first caudal actuator 144 and second caudal actuator 145 of caudal member 140, discussed above. In some embodiments, the motion of first adjustable body 127 is controlled by first cranial actuator 124 or second cranial actuator 125 in scope and manner substantially different than the control of second adjustable body 147 by first caudal actuator 144 or second caudal actuator 145. In some embodiments, the manner of activation employed by first cranial actuator 124, second cranial actuator 125, first caudal actuator 144, and second caudal actuator 145 is substantially the same. In some embodiments, first cranial actuator 124 or first caudal actuator 144 is a unitary actuator, wherein either first cranial actuator 124 or first caudal actuator 144 positions both cranial adjustable body 127 and caudal adjustable body 147 simultaneously along line AP. In some embodiments, second cranial actuator 125 or second caudal actuator 145 is a unitary actuator, wherein either second cranial actuator 125 or second caudal actuator 144 positions both cranial adjustable body 127 and caudal adjustable body 147 simultaneously along line L.

In some embodiments, adjustments are performed non-surgically by remotely adjusting any one or more of first cranial actuator 124, second cranial actuator 125, first caudal actuator 144, or second caudal actuator 145 in any combination based upon data generated from an internal cranial stress monitoring device (not shown in the Figures), an internal caudal stress monitoring device (not shown in the Figures), or data generated from both the internal cranial stress monitoring device and the internal caudal stress monitoring device. In some embodiments, either or both the internal cranial stress monitoring device and the internal caudal stress monitoring device are coupled to IVD replacement device 100. In some embodiments, either or both the internal cranial stress monitoring device and the internal caudal stress monitoring device are not coupled to IVD replacement device. Either or both of the internal cranial stress monitoring device and the internal caudal stress monitoring device may be mechanically coupled to an intervertebral disc, a vertebral body, an intervertebral facet joint, a vertebral lamina, a vertebral pedicle, or any other vertebral or intervertebral anatomic structure adjacent to or remote from the spinal level of total IVD replacement device 100 insertion, without limitation. This use of stress monitoring devices for internal stress monitoring, in some embodiments, directs and allows for non-surgical adjustments of cranial adjustable body 127 or caudal adjustable body 147 to be performed at any time, according to changes in force distribution along the anterior or posterior spinal columnar elements to create and maintain a favorable distribution of forces within the spinal column.

Figure 2:
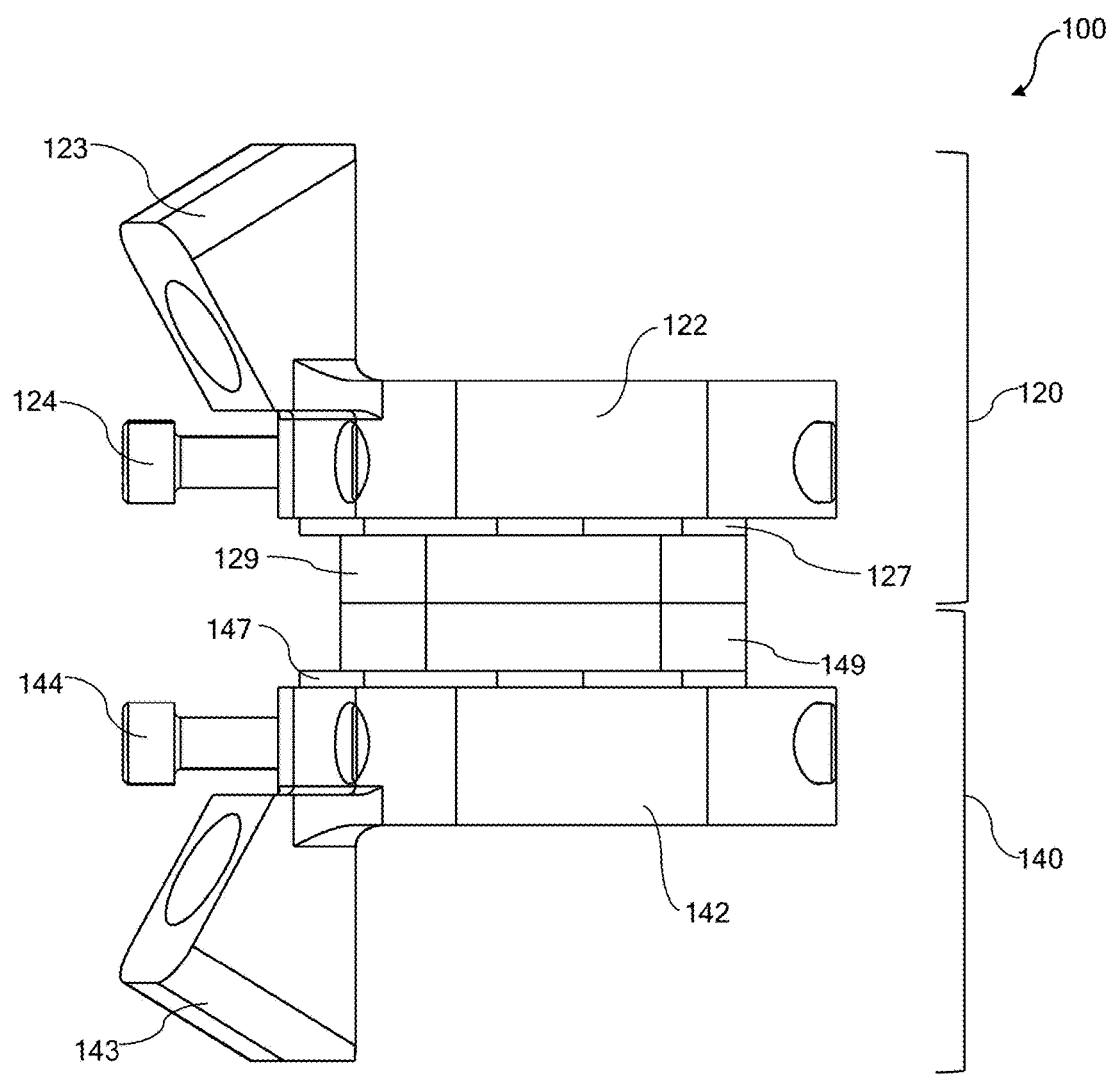
FIG. 2 is a left side view of a total intervertebral disc replacement device.

FIG. 2 is a left side view of total IVD replacement device 100. As shown in FIG. 2, cranial member 120 contacts caudal member 140 at the interface between cranial articular surface 129 and caudal articular surface 149. Also shown in FIG. 2 is a cranial screw strut 123 of cranial base member 122 and a caudal screw strut 143 of caudal base member 142. Cranial screw strut 123 and caudal screw strut 143 in the embodiment shown direct a bone screw into a vertebral body at an angle suitable to create a force component tending to secure each base member upward or downward (i.e. cranially or caudally) against its corresponding vertebral body.

FIG. 2 shows the small portion of cranial adjustable body 127 and caudal adjustable body 147 extending from a cranial base body 122 and caudal base body 142 respectively. In the embodiment shown in the figures, this exposed portion of each adjustable body comprises a flange which contacts a sliding surface of the corresponding base body. Cranial adjustable body 127 comprises a cranial flange 128 and second adjustable body 147 comprises a caudal flange 148. The full shape of cranial adjustable body 127 and caudal adjustable body 147, including cranial flange 128 and caudal flange 148, is shown in the exploded drawing figures (FIG. 8-FIG. 10) discussed herein below.

FIG. 2 also shows first cranial actuator 124 and first caudal actuator 144 partially engaged within cranial base member 122 and caudal base member 142 respectively. First actuator 124 and second actuator 144 are shown fully engaged within the corresponding base members 122 and 142 by FIG. 1(D). In this and some other embodiments, first cranial actuator 124 and first caudal actuator 144 are bolts which are accessed from an anterior (front-side) position. This facilitates activating the corresponding adjustable body in the A/P axis. Some embodiments may employ first actuator 124, second actuator 144, or both accessed from a lateral position to facilitate activating the corresponding adjustable body on the lateral axis. Other actuator apparatuses may be used, such as, for example, cams, levers, cantilevered members, an apparatus comprising a solenoid, other electronic apparatus, or a hydraulic apparatus. Any suitable apparatus for causing movement of an adjustable body, controlling movement of an adjustable body, or simultaneously both causing and controlling movement of cranial adjustable body 127 or caudal adjustable body 147 within a base body 122 or a base body 142 respectively are used in some embodiments of the invention.

Figure 3:
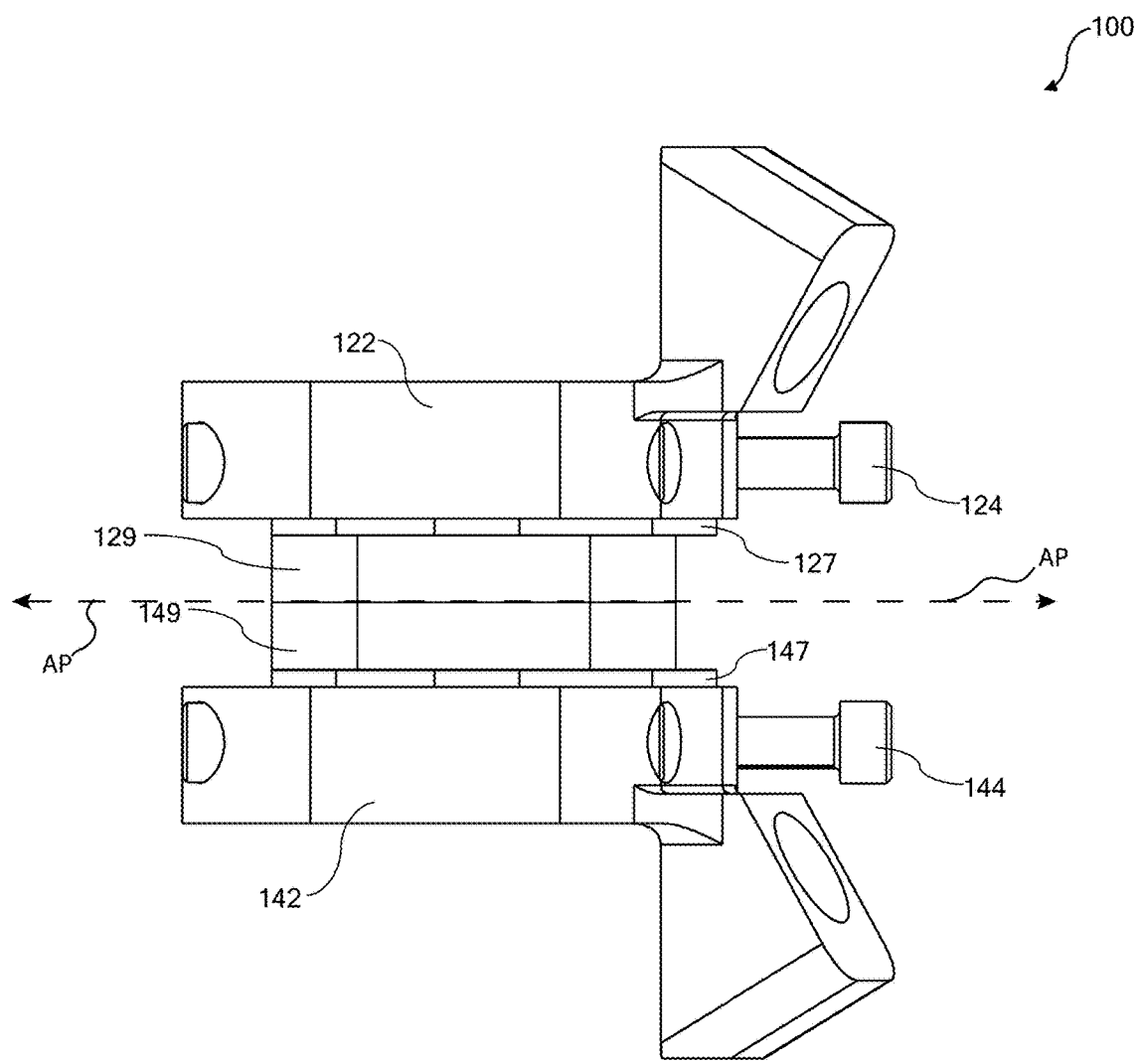
FIG. 3 is a right side view of a total intervertebral disc replacement device.

FIG. 3 is a right side view of total IVD replacement device 100, corresponding to the left side view shown in FIG. 2 and described above. In the embodiments shown by the figures, there is left-right symmetry. This is not meant to be limiting. In some embodiments, asymmetry between the left side and the right side of total IVD replacement device 100 may be present. Additionally, FIG. 3 shows anteroposterior axis line AP.

Figure 4:
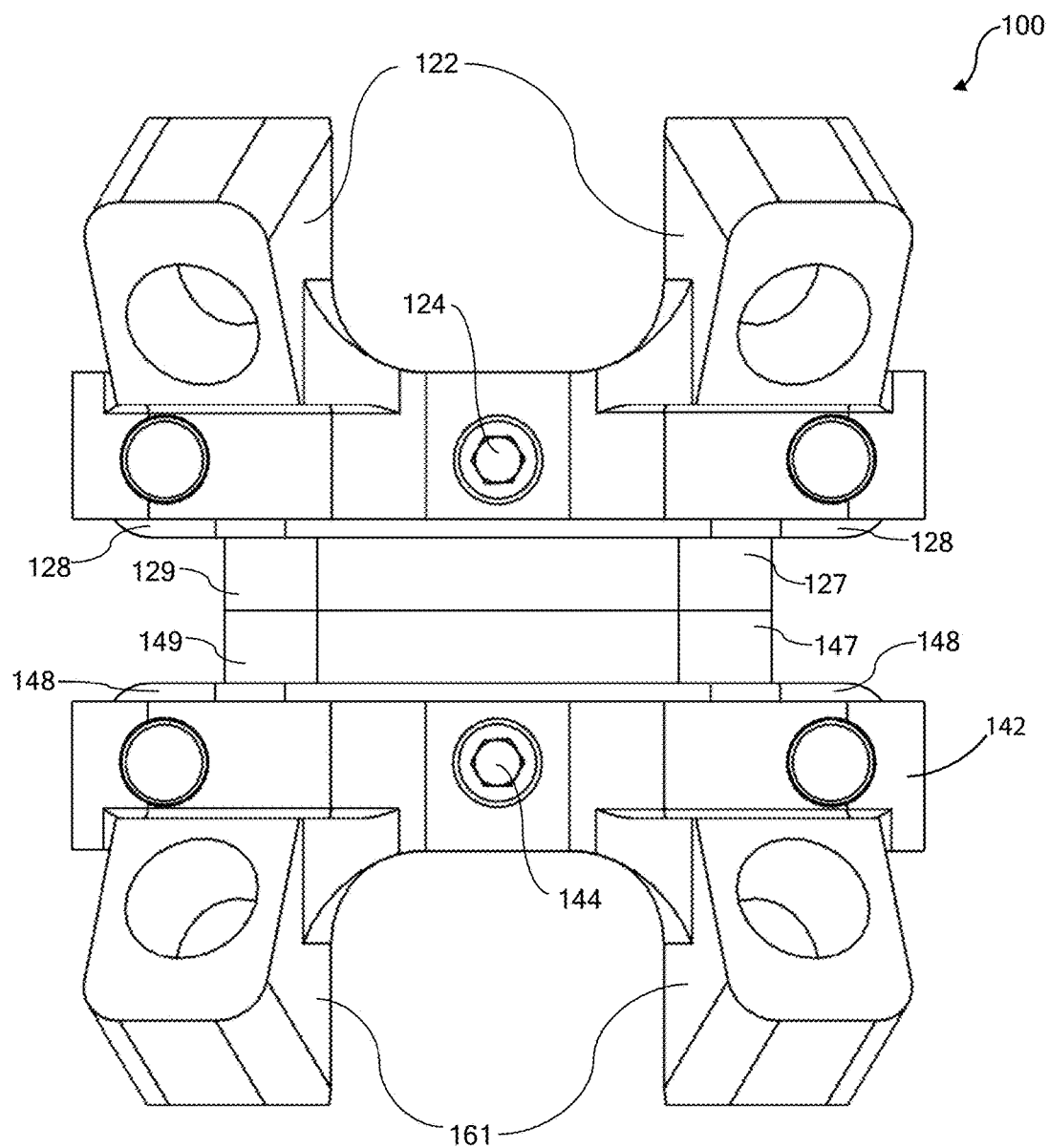
FIG. 4 is a front (anterior) view of a total intervertebral disc replacement device.

FIG. 4 is a front (anterior) view of total IVD replacement device 100. A corresponding view of an implanted total IVD replacement device 100 mentioned above is shown by FIG. 1(D). In the embodiment shown by FIG. 4, total IVD replacement device 100 projects backward (posteriorly) into the intervertebral space, replacing the excised IVD, at the level where total IVD replacement device 100 is implanted in the spinal column. First cranial actuator 124 and first caudal actuator 144 are shown, along with the midline positioning of each actuator in the illustrated embodiment. Also shown in FIG. 4 are caudal screw struts 161 oriented at an angle for engaging cranial bone screws 112. First flange 128 of cranial adjustable body 127 and second flange 148 of caudal adjustable body 147 are also shown.

Figure 5:
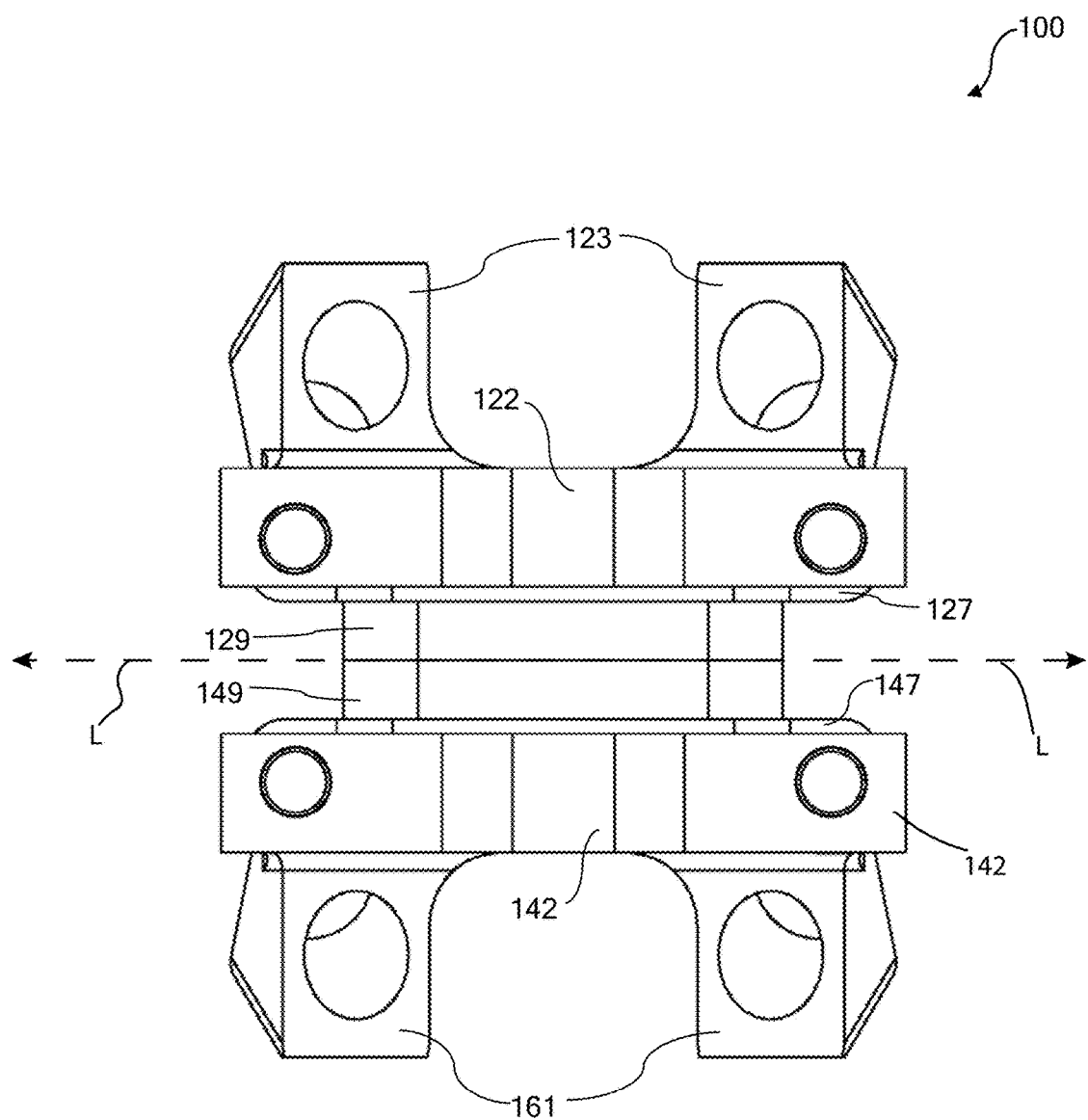
FIG. 5 is a back (posterior) view of a total intervertebral disc replacement device.

FIG. 5 shows a back (posterior) view of total IVD replacement device 100. In the embodiment shown in FIG. 5, with the exception of cranial screw struts 123 and caudal screw struts 161, all visible surfaces of the device in the figure are contained within the intervertebral space, cranial vertebral body, and caudal vertebral body when total IVD replacement device 100 is implanted in a spinal column. Additionally, FIG. 5 shows lateral axis line L.

Figure 6:
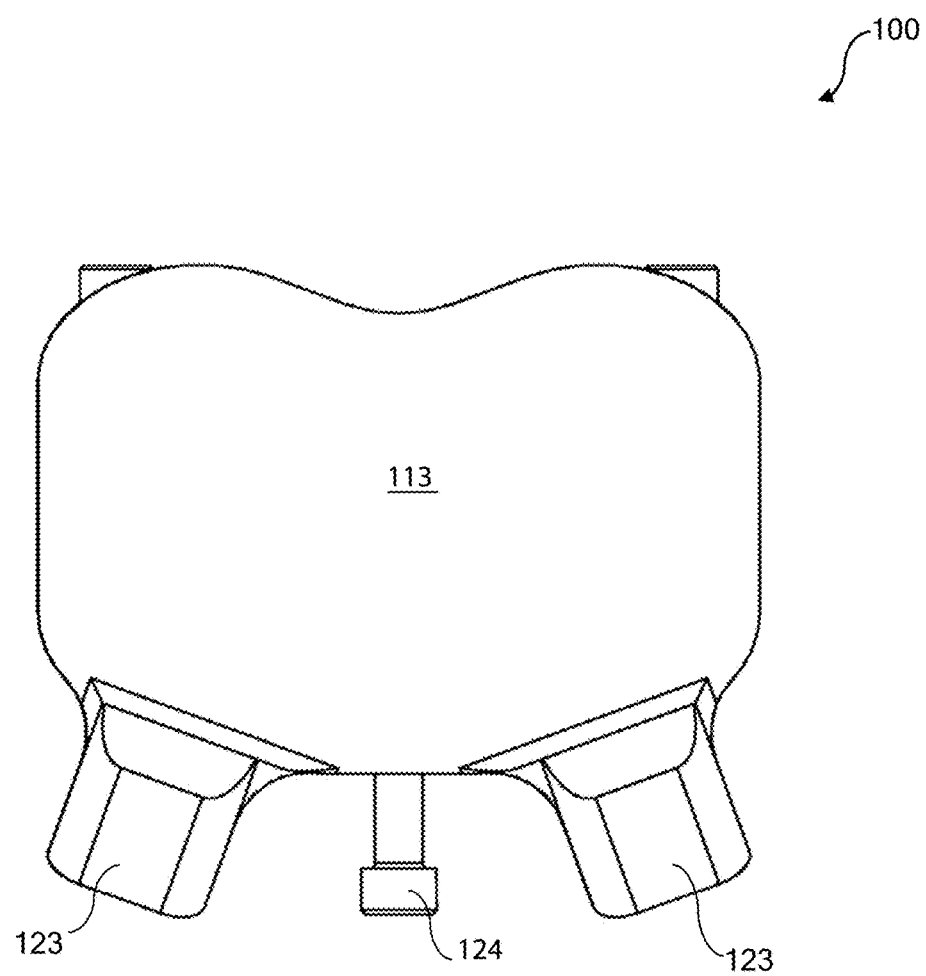
FIG. 6 is a top view of a total intervertebral disc replacement device.

FIG. 6 shows a top view of total IVD replacement device 100. Cranial base body 122, cranial screw struts 123 and first cranial actuator 124 are the only designated structures seen in this view. Of note, cranial base member 122 comprises cranial adhesive surface 113. Cranial adhesive surface 113 and caudal adhesive surface 163 shown in FIG. 7, each present a broad, flat surface for contacting the caudal aspect or cranial aspect respectively of a vertebral body when implanted into the resected IVD space. In some embodiments, cranial base body 122, caudal base body 142, or both elements are formed from a sufficiently porous material, such as tantalum or tantalum-ceramic, for example, to enhance penetration of bone cement and/or ingrowth of bone. In some embodiments, the combination of porous material and a relatively large surface area contributes to stable and durable fixation of cranial base body 122 and caudal base body 142 to the corresponding vertebral bodies.

Figure 7:
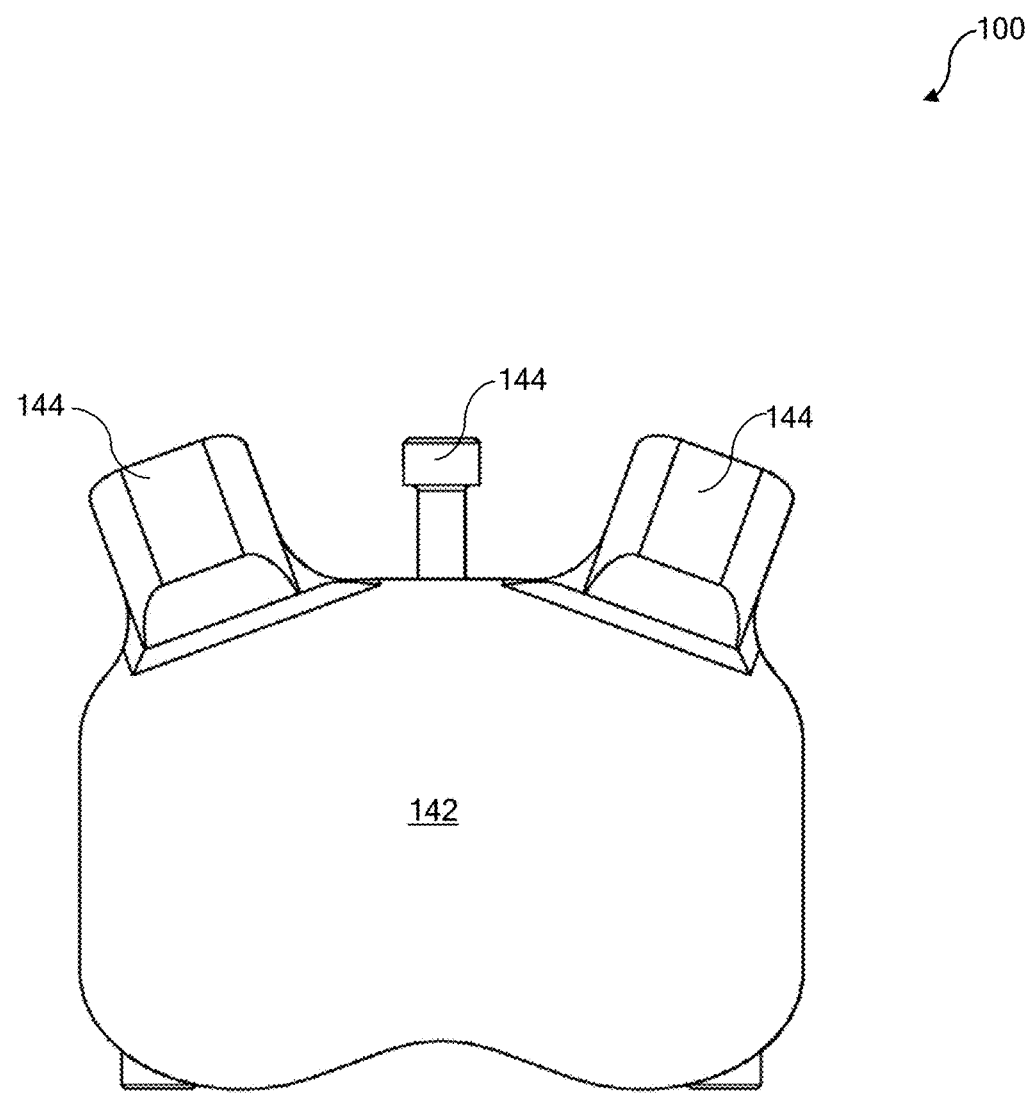
FIG. 7 is a bottom view of a total intervertebral disc replacement device.

FIG. 7 shows a bottom view of total IVD replacement device 100. As shown by FIG. 6 and FIG. 7, some embodiments of total IVD replacement device 100 present a similar profile from the top or the bottom.

Figure 8:
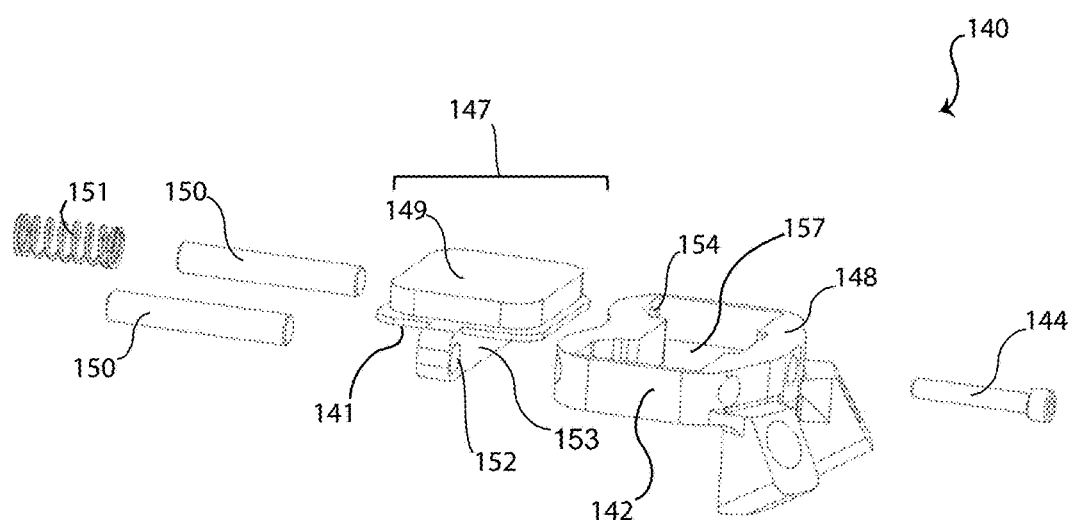
FIG. 8 is an exploded perspective view of a caudal member of a total intervertebral disc replacement device.
Figure 9:
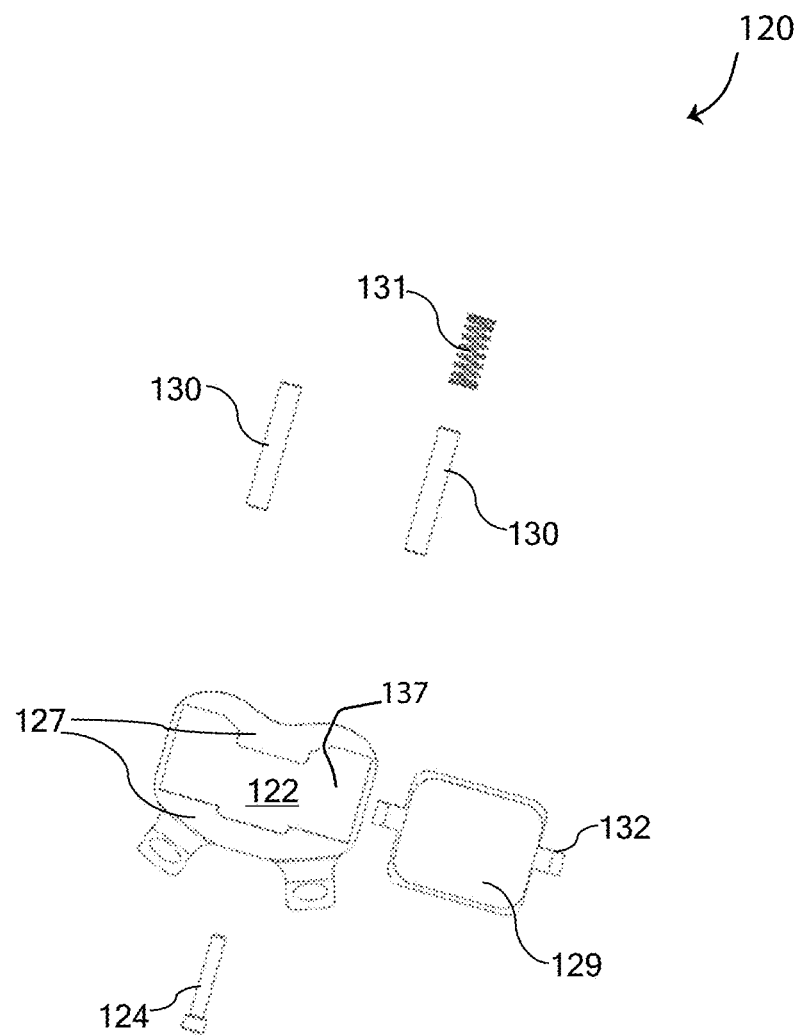
FIG. 9 is a bottom exploded view of a cranial member of a total intervertebral disc replacement device.
Figure 10:
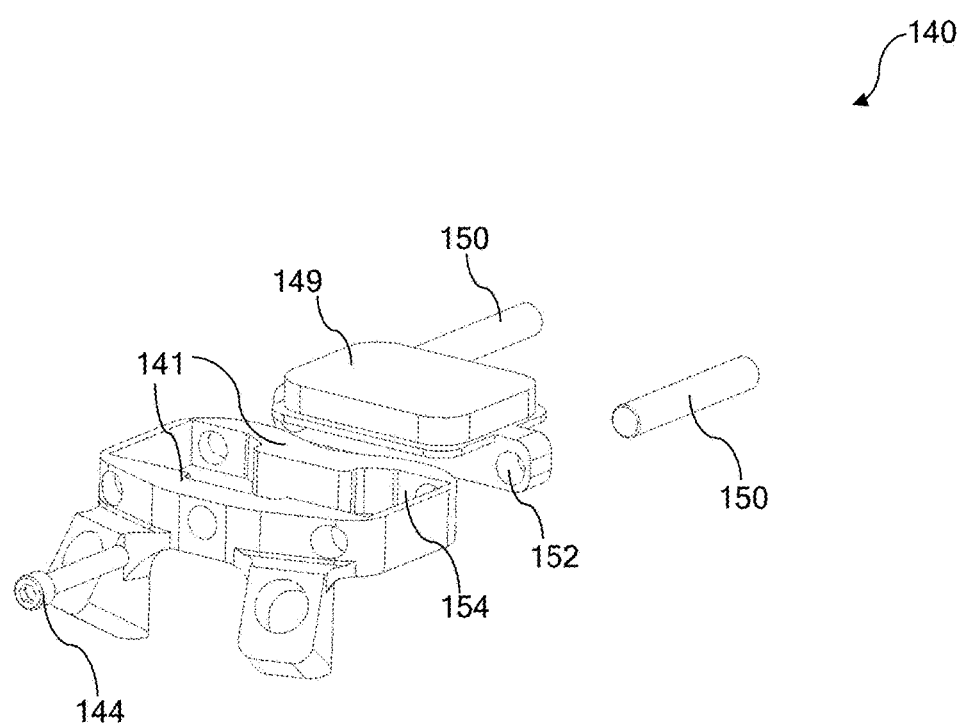
FIG. 10 is an exploded perspective view of a caudal member of a total intervertebral disc replacement device.

Exploded views of FIG. 8-FIG. 10 demonstrate elements of one non-limiting example embodiment for positioning (moving and/or fixing in position) an adjustable body of total IVD replacement device 100 wherein the components shown have been discussed with regard to FIGS. 1-7. The listed elements comprising caudal member 140, or cranial member 120, comprise a system wherein a dynamic COR is created. The joint interface between cranial articular surface 129 and caudal articular surface 149 is movable such that the natural distribution of forces during anteroposterior flexion, lateral bending, and axial rotation of the vertebral bodies along the spinal axis on either side of the implanted total IVD replacement device 100 is preserved.

Different embodiments of total IVD replacement device 100 create a dynamic COR in slightly different ways, according to the movement characteristics and forces present at the IVD joint replacement level in the spinal column. For example, in some embodiments, the position of caudal adjustable body 147 relative to caudal base body 142 adjusts by moving along a first caudal track 150 in the caudal axis AP. In some embodiments, the position of caudal adjustable body 147 relative to caudal base body 142 additionally adjusts by moving along a second caudal track in the caudal axis L, wherein caudal adjustable body 147 "floats" in a plane formed by the two coplanar lines caudal axis AP and caudal axis L. First caudal track 150 may be any track, such as a pin-track as shown in FIG. 7 and FIG. 8. Alternatively, first caudal track may be a groove in caudal base body 142 that engages with a shape corresponding to a tongue on caudal adjustable body 147. In some embodiments, the groove is located on caudal adjustable body 147 and the shape comprises caudal base body 142. In some embodiments, other pin-and-groove track mechanisms are used.

A similar arrangement of elements comprises cranial member 120, such cranial adjustable body 127 moves in relation to cranial base body 122 causing the position of cranial articular surface 129 of cranial adjustable body 127 to correspond with caudal articular surface 140 of caudal adjustable body 147. In some embodiments, cranial member 120 comprises a first cranial actuator 124 that adjusts a position of cranial adjustable body 127 along cranial axis AP by controlling movement along cranial axis AP or fixing the position of cranial adjustable body 127 along cranial axis AP. In some embodiments, cranial member 120 comprises a second cranial actuator 125 that adjusts a position of cranial adjustable body 127 along cranial axis L by controlling movement along cranial axis L or fixing the position of cranial adjustable body 127 along cranial axis L. In some embodiments, a first cranial biasing member 131 biases cranial adjustable body 127 against first cranial actuator 124. First cranial biasing member 131 may be a compression spring, in some embodiments. In some embodiments, first cranial biasing member 131 may be a mechanical biasing member other than a compression spring. In some embodiments, first cranial biasing member 131 may be a solenoid or similar electrically-activated magnetic biasing device.

In some embodiments, a first caudal actuator 144 controls movement of caudal adjustable body 147 in one direction along caudal axis AP. In some embodiments, first caudal actuator 144 fixes caudal adjustable body 147 in a fixed position, wherein adjustment of first caudal actuator 144 determines the position of fixation of caudal adjustable body 147 along caudal axis AP. In some embodiments, a first caudal biasing member 151 biases caudal adjustable body 147 against first caudal actuator 144. First caudal biasing member 151 may be a compression spring, in some embodiments and in the embodiment shown in FIG. 8 and FIG. 9. In some embodiments, first caudal biasing member 151 may be a mechanical biasing member other than a compression spring. In some embodiments, first caudal biasing member 151 may be a solenoid or similar electrically-activated magnetic biasing device.

Such elements may comprise caudal member 140, cranial member 120, both, or neither in embodiments of the invention. In some embodiments, a positioning/fixing apparatus other than shown in the drawing figures may be used. Different or similar elements may comprise caudal member 140 and cranial member 120 in some embodiment of the invention. In some embodiments, adjustment of any one actuator, such as first cranial actuator 124, second cranial actuator 125, first caudal actuator 144, or second caudal actuator 145 simultaneously and correspondingly adjusts, limits, or fixes the position of both cranial articular surface 129 of cranial adjustable body 127 and caudal articular surface 149 of caudal adjustable body 147. In some embodiments, adjustment of any two actuators correspondingly adjusts, limits, or fixes the position of both cranial articular surface 129 of cranial adjustable body 127 and caudal articular surface 149 of caudal adjustable body 147.

In the embodiment shown in FIG. 8, and some other embodiments, caudal adjustable body 147 comprises a caudal rib 153 coupled to caudal flange 148 opposite caudal articular surface 149. When assembled, caudal rib 153 is enveloped within caudal base body 142. Caudal flange 128 engages a caudal sliding surface 141 of caudal base body 142; correspondingly, cranial flange 128 engages a cranial sliding surface 134 of cranial base body 122. In the embodiments shown in FIG. 8 and other drawing figures, caudal rib 153 comprises a caudal track guide 152. In some embodiments, two caudal track guides 152 each engage a corresponding caudal track 150. Caudal track 150 is coupled to caudal base body 142. In some embodiments, a first cranial track 130 is similarly coupled to cranial base body 142. In the embodiment shown in FIG. 8, first caudal biasing member 151 also engages first caudal track 150, although this is not meant to be limiting. When assembled, first caudal track 150 and first caudal biasing member 151 are located within an inner volume of caudal base body 141 such that first caudal biasing member 151 is constrained and partially compressed between first caudal blocking surface 154 and second rib 153. A similar mechanism for cranial member 120 comprising a first cranial track 130, a first cranial biasing member 131, cranial base body 122, a first cranial blocking surface 134, and a first cranial rib 133. First cranial actuator 124 or first caudal actuator 144 engage cranial rib 133 or caudal rib 153 opposite first cranial biasing member 131 or first caudal biasing member 151 respectively such that first cranial actuator 124 or first caudal actuator 144 and first cranial actuator 131 or first caudal actuator 151 exert opposing forces against cranial rib 133 or caudal rib 153 respectively. These opposing forces operate to stabilize cranial adjustable body 127 or caudal adjustable body 147 in a position governed by the position of first cranial actuator 124 or first caudal actuator 144 respectively. The foregoing example of an apparatus for positioning an adjustable body of total IVD replacement device 100 is not meant to be limiting. Any similar or alternative but suitable means for adjusting the position of cranial articular surface 129 or caudal articular surface 149 relative to cranial base body 122 or caudal base body 142 respectively of total IVD replacement device 100 can be used.

FIG. 9 is a bottom (caudal) view of elements of a disassembled cranial member of a total IVD replacement device. FIG. 9 shows cranial base body 122 and cranial adjustable body 127, two first cranial tracks 130, first cranial biasing member 131 and first cranial actuator 124, in a non-limiting example embodiment.

FIG. 10 is an additional exploded perspective view of a caudal member of a total IVD replacement device. Similar to FIG. 8 discussed in detail herein above, FIG. 10 shows elements comprising caudal member 140, including first caudal track 150 and first caudal track guide 152, wherein caudal adjustable body 147 moves along caudal axis AP (not shown). First caudal biasing member 151 is not shown in this figure.

Figure 11:
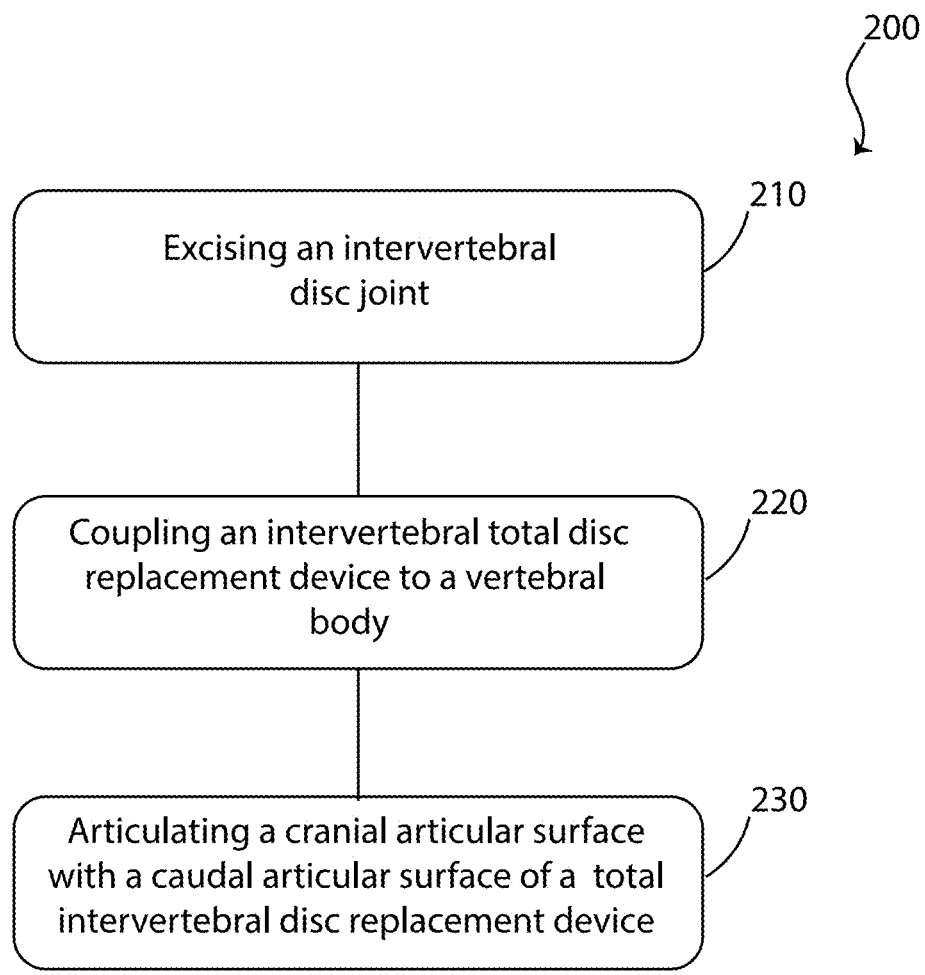
FIG. 11 is a flowchart of a method of inserting a total intervertebral disc replacement device in a patient.

FIG. 11 is a flowchart diagram of a method 200 of surgically inserting an total IVD replacement device into a patient. Method 200 comprises an excising step 210, a coupling step 220, and an articulating step 230. Excising step 210 comprises surgically removing the IVD from an intervertebral space, using established surgical techniques known in the art. In some embodiments, excising step additionally comprises excising a portion of each vertebral body bounding the excises IVD intervertebral space cranially and caudally to increase the space available for insertion of the total IVD replacement device.

Coupling step 220 comprises coupling a total IVD replacement device to a vertebral body. In some embodiments, coupling step comprises utilizing a commercially available bone screw designed for fixing a hardware device to a vertebral body to fix a cranial base body or a caudal base body of the total IVD replacement device to the corresponding vertebral body. In some embodiments, coupling step 220 comprises the use of a biocompatible adhesive bone cement, such as polymethyl-methacrylate, or the like. In some embodiments, coupling step 220 comprises both the use of a bone screw and an adhesive. In some embodiments, coupling step 220 comprises the use of an alternative orthopedic fixation device other than a bone screw.

Articulating step 220 of method 200 comprises articulating a cranial articular surface and a caudal articular surface of a total IVD replacement device. In some embodiments, articulating step 220 is performed prior to coupling step 220. In some embodiments, articulating step 220 is performed following coupling step 220, with or without execution of additional intervening steps, in some embodiments.

Figure 12:
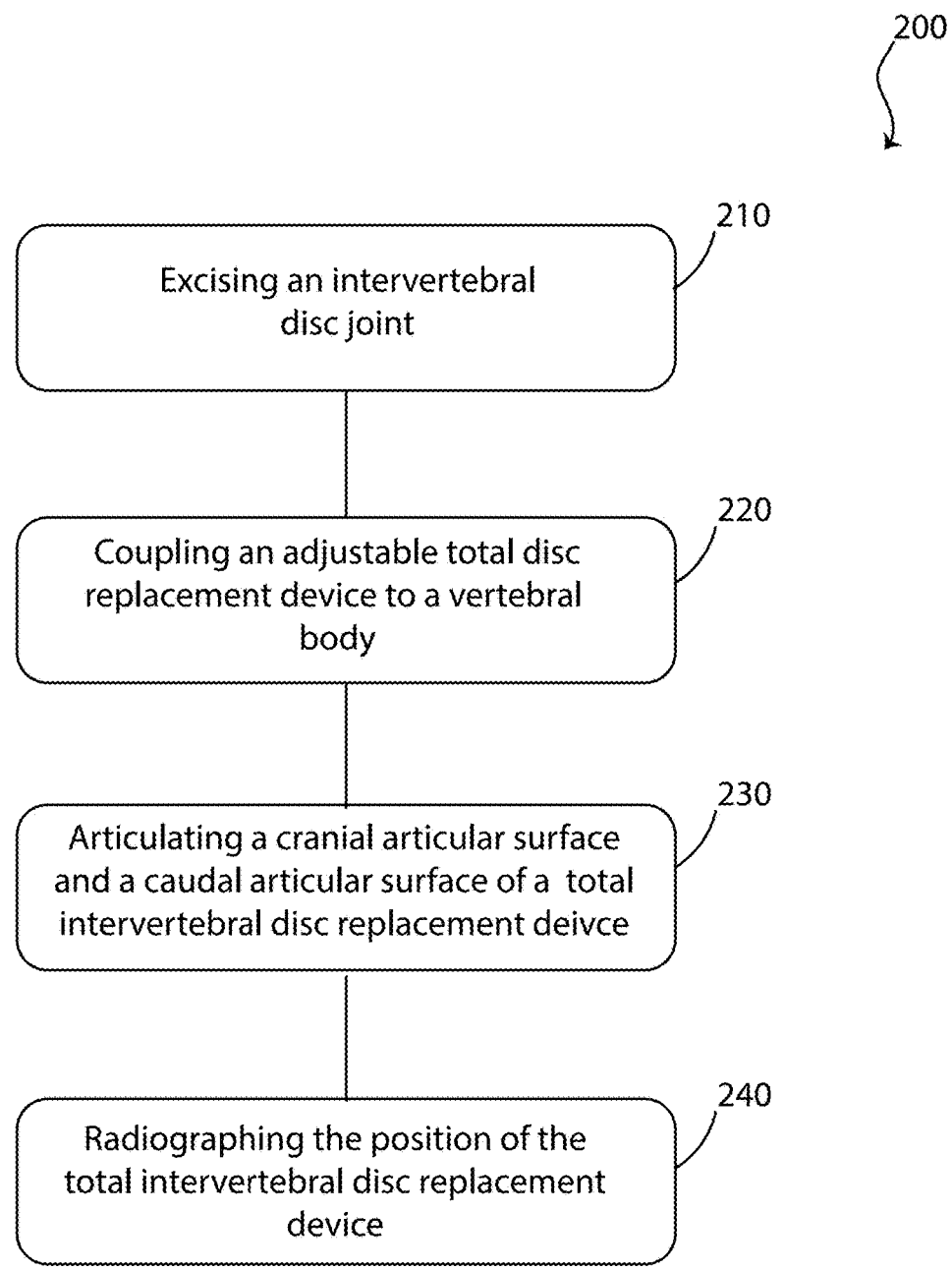
FIG. 12 is a flowchart of an alternative embodiment of a method of inserting a total intervertebral disc replacement device in a patient.

FIG. 12 is a flowchart diagram an alternative embodiment of method 200. FIG. 12 shows an additional radiographing step 240. Radiographing step 240 comprises radiographing the position of the total IVD replacement device following coupling step 220 and articulation step 230. Radiographing step 240 is performed utilizing established techniques known in the art and is useful to confirm proper positioning of total IVD replacement device 100 in the patient, prior to completing the surgical procedure.

Figure 13:
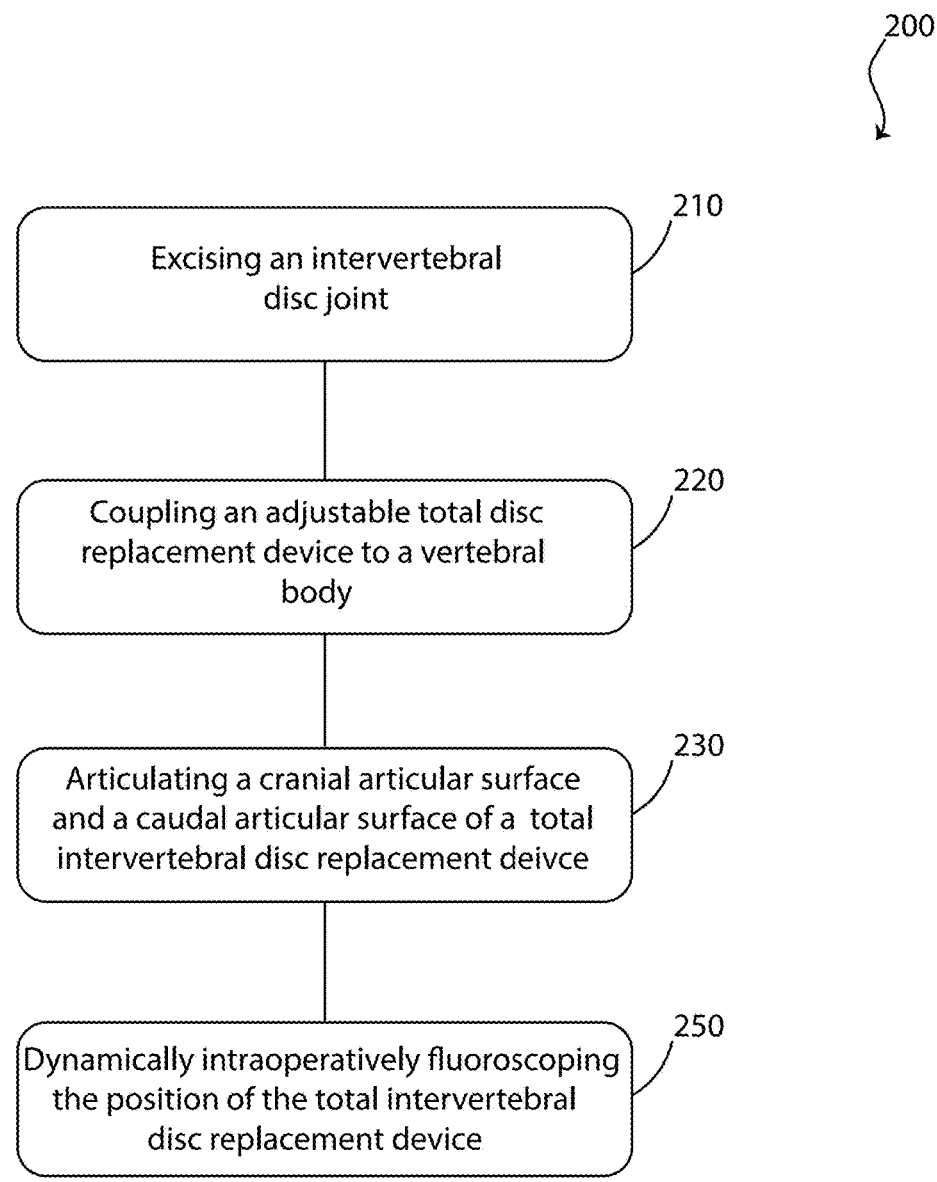
FIG. 13 is a flowchart of an additional alternative embodiment of a method of inserting a total intervertebral disc replacement device in a patient.

FIG. 13 is a flowchart diagram of an additional alternative embodiment of method 200. FIG. 13 shows an additional fluoroscoping step 250. Fluoroscoping step 250 comprises dynamically intraoperatively fluoroscoping the position of the total IVD replacement device. The use of intraoperative fluoroscopy is important, in some embodiments, to evaluate how the position of coupled total IVD replacement device 100 affects movement of intervertebral joints through the spinal column above and below inserted total IVD replacement device 100. Evidence of asynchronous motion, asymmetrical motion, and unbalanced force distribution caused by an sub-optimally positioned or maladjusted total IVD replacement device is visible upon fluoroscopic evaluation during flexion-extension, lateral bending, and axial rotation, in some embodiments. The surgeon is then able to discover sub-optimal positioning or adjustment of the total IVD replacement device and attempt to correct the position or adjustment while the patient remains under anesthesia in the operating room.

Figure 14:
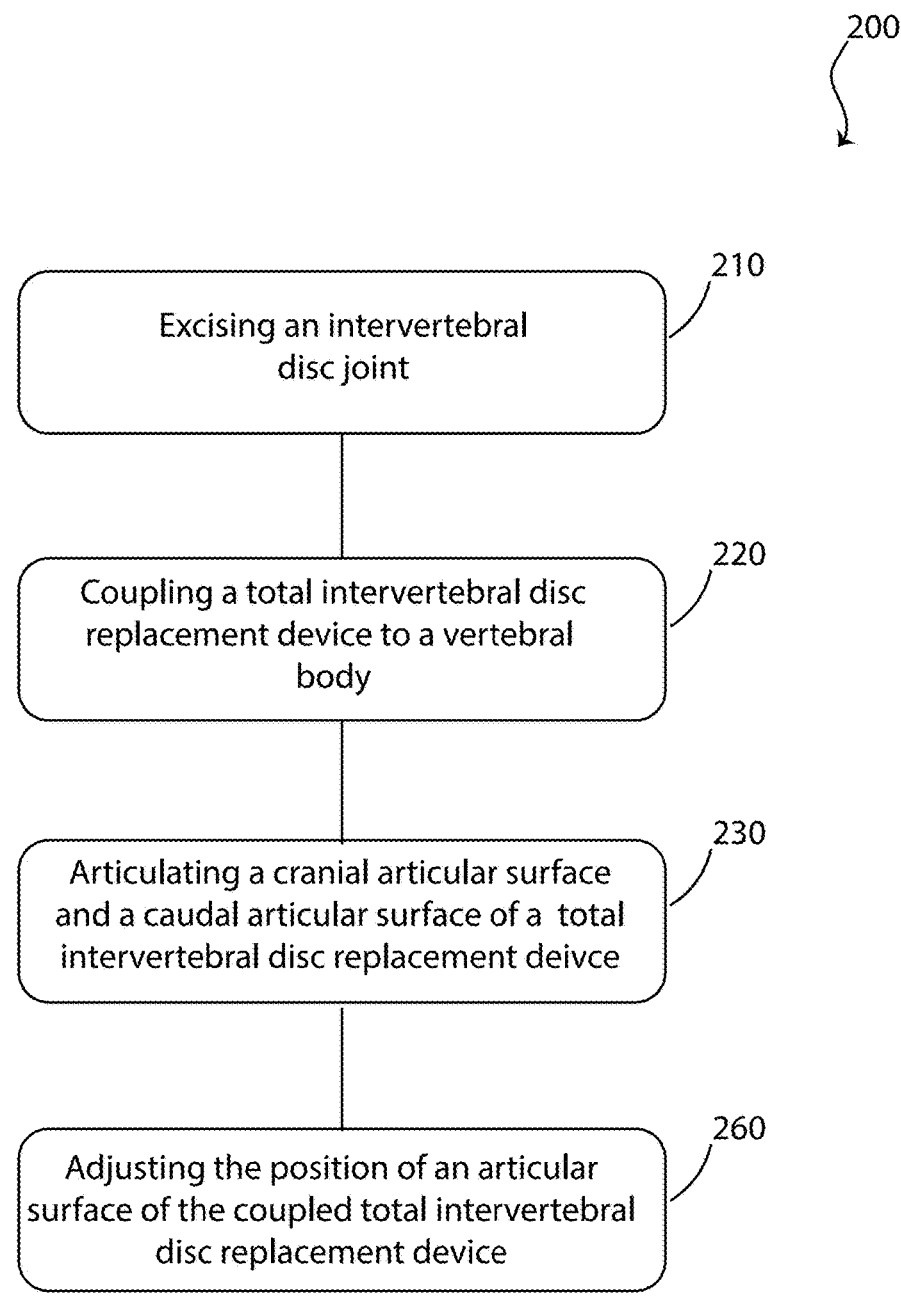
FIG. 14 is a flowchart of an additional alternative embodiment of a method of inserting a total intervertebral disc replacement device in a patient.

FIG. 14 is a flowchart diagram yet another alternative embodiment of method 200. FIG. 14 shows an additional adjusting step 260. Adjusting step 260 comprises adjusting the position of an articular surface of the coupled total IVD replacement device. In some embodiments, adjusting step 260 comprises adjustment of an actuator to adjust, move, or fix the position of the articular surface. In some embodiments, adjusting step 260 is performed following radiographing step 240 or fluoroscoping step 250. In some embodiments, adjusting step 260 and fluoroscoping step 215 are alternatively and repeatedly performed until the position of the articular surface is optimized by the operating surgeon.

In some embodiments, adjusting step 260 is performed at a time after the patient leaves the operating room. In some embodiments, adjusting step 260 is performed by a healthcare provider other than the operating surgeon, in a remote place and at a remote time from the surgical procedure performed in a hospital to insert total IVD replacement device 100 in the patient. For example, in some embodiments, adjustments are performed non-surgically by remotely adjusting any one or more of first cranial actuator 124, second cranial actuator 125, first caudal actuator 144, or second caudal actuator 145 in any combination based upon data generated from an internal cranial stress monitoring device (not shown in the Figures), an internal caudal stress monitoring device (not shown in the figures), or date generated from both the internal cranial stress monitoring device and the internal caudal stress monitoring device.

Experimental Example and Results

In the course of developing various embodiments of the invention, experiments were undertaken to determine the biomechanical effects of cervical fixed-COR TDR device position variations on inter-vertebral body motion and vertebral load sharing. To develop and test a working prototype of some embodiments of the invention, an experimental model was used. In this model, TDR was performed in fresh cadaveric human donor spines at the C5-C6 position. A commercially available 5 mm M TDR device coupled to an embodiment of the invention was implanted. Implantation required a full C5-C6 disc In this and other embodiments, the A/P endplate position is adjustably controlled with a center set screw, wherein two full screw rotations translates the endplate position by 1 mm in the A/P plane.

In one experimental example, fresh, un-embalmed cadaver spine specimens comprising integrated segments C3-T1 from five human donors (three male and two female, mean age±standard deviation of 49.2±11.2 years) were used. Stain gauges were attached to the right and left lamina of C5 to monitor vertebral load sharing across the C5/C6 facet joints immediately above the TDR index level (C5-C6). The specimens were tested quasi-statically using pure moments (1.5 Newton-meters) in flexion-extension ("FE"), right and left axial rotation ("AR"), and right and left lateral bending ("LB") in the following configurations: 1) normal/intact (no TDR); 2) centered TDR; 3) TDR positioned 2 millimeters ("MM") anteriorly; and 4) TDR positioned 2 mm posteriorly. The testing order in configurations 2, 3, and 4 above was randomized among the specimens. Anteroposterior ("A/P") device positions were controlled on custom designed and fabricated inferior and superior implant base plates with implant positions verified using X-ray fluoroscopic A/P and lateral views. Collected data included range of motion ("ROM"), lax zone/stiff zone, location of COR, angular coupling, and changes in surface strain indicating changes in load sharing across the anterior (vertebral bodies/IVD joints) and posterior (facet joints) elements of the vertebral column. The effects of TDR position variations were analyzed by comparing the changes from normal and using RM-ANOVA with a p-value of 0.05.

Results showed that the A/P TDR position variations had a greater effect on the ROM during FE than during LB and AR, however the changes were not statistically significant in any direction of motion. The effects of TDR position variations on coupled motion, including AR during LB and LB during AR, were not significant. The axis of rotation shifted in the direction of the changed TDR position.

There were, however, notable changes in laminar strains, indicating changes in facet loads within the posterior column. These results were interpreted to show that although A/P position variations of greater than 2 mm of a cervical TDR at the C5-C6 level have a fixed COR not significantly affected by the ROM or coupled motion, IAR and laminar strains show significant load-sharing changes between the anterior and posterior spinal columns via the facet joints.

An total IVD replacement device has been described. Preliminary testing of a prototype of some embodiments of the invention suggests the total IVD replacement device performs well in the experimental model and provides superior versatility compared to TDR devices currently available and described in the art. The total IVD replacement device is surgically implanted to replace an IVD damaged by disease, trauma, or other degenerative process. Elements of the invention enable adjustment of the relative positions of the joint's articular surfaces, allowing for optimization of load distribution between the anterior and posterior spinal elements, thus increasing stability and providing optimal performance specific to the age, physical parameters, and activity requirements of an individual patient.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A total intervertebral disc replacement device comprising:
   a cranial member, comprising:
      a cranial base body comprising a first recess defining an inner volume having a perimeter;
      a cranial adjustable body coupled to the cranial base body within the first recess and moveable within the perimeter of the first recess in a non-fixed position, wherein the cranial adjustable body adjusts along a cranial AP axis with respect to the cranial base body;
      a cranial articular surface coupled to the cranial adjustable body;
   a caudal member, comprising
      a caudal base body comprising a second recess defining an inner volume having a perimeter;
      a caudal adjustable body coupled to the caudal base body within the second recess and moveable within the perimeter of the second recess in a non-fixed position, wherein the caudal adjustable body adjusts along a caudal AP axis with respect to the caudal base body and wherein the caudal AP axis is parallel to the cranial AP axis; and
      a caudal articular surface coupled to the caudal adjustable body, wherein the cranial articular surface and the caudal articular surface are fashioned into complimentary shapes that moveably engage one another; and
   a joint comprising the complimentary shapes of the cranial articular surface and the caudal articular surface
   wherein the joint has a floating center of rotation with respect to at least one of the cranial base body or the caudal base body.

2. The total intervertebral disc replacement device of claim 1, wherein the cranial adjustable body is slidably coupled to the cranial base body and the caudal adjustable body is slidably coupled to the caudal base body.

3. The total intervertebral disc replacement device of claim 1, wherein the cranial articular surface comprises a concave curvature and the caudal articular surface comprises a convex curvature, wherein the convex curvature corresponds to the concave curvature.

4. The total intervertebral disc replacement device of claim 1, further comprising:
   a first cranial actuator coupled to the cranial base body and engaging the cranial adjustable body; and
   a first caudal actuator coupled to the caudal base body and engaging the caudal adjustable body.

5. The total intervertebral disc replacement device of claim 4, wherein the first cranial actuator controls motion of the cranial adjustable body relative to the cranial base body along the cranial AP axis, and the first caudal actuator controls motion of the caudal adjustable body relative to the caudal base body along the caudal AP axis.

6. The total intervertebral disc replacement device of claim 4, wherein the first cranial actuator adjusts the position of the cranial adjustable body relative to the cranial base body along the cranial AP axis, and the first caudal actuator adjusts the position of the caudal adjustable body relative to the caudal base body along the caudal AP axis.

7. The total intervertebral disc replacement device of claim 1, further comprising a unitary actuator coupled to the cranial base body, and engaging the cranial adjustable body, wherein activation of the unitary actuator positions the joint relative the cranial base body.

8. The total intervertebral disc replacement device of claim 1, further comprising a unitary actuator coupled to the caudal base body, and engaging the caudal adjustable body, wherein activation of the unitary actuator positions the joint relative the caudal base body.

9. The total intervertebral disc replacement device of claim 1, further comprising
   a first cranial actuator coupled to the cranial base body and engaging the cranial adjustable body; and
   a first caudal actuator coupled to the caudal base body and engaging the caudal adjustable body, wherein activation of the first cranial actuator positions the joint relative the cranial base body and activation of the first caudal actuator positions the joint relative to the caudal base body.

10. The total intervertebral disc replacement device of claim 1, further comprising an AP movement mechanism comprising:
   a first cranial track wherein a long axis of the cranial track is parallel to the cranial AP axis;
   a first cranial biasing member engaging the cranial adjustable body, wherein the first cranial biasing member biases motion of the cranial adjustable body in a direction along the cranial AP axis relative to the cranial base body;
   a first caudal track wherein a long axis of the caudal track is parallel to the caudal AP axis; and
   a first caudal biasing member engaging the caudal adjustable body, wherein the first caudal biasing member biases motion of the caudal adjustable body in a direction along the caudal AP axis relative to the caudal base body.

11. A total intervertebral disc replacement device comprising
   a cranial member, comprising:
      a cranial base body comprising a first recess defining an inner volume having a perimeter;
      a cranial adjustable body slidably coupled to the cranial base body within the first recess and moveable within the perimeter of the first recess in a non-fixed position, wherein the cranial adjustable body slides within a cranial plane with respect to the cranial base body;
      a cranial articular surface coupled to the cranial adjustable body;
   a caudal member, comprising
      a caudal base body comprising a second recess defining an inner volume having a perimeter;
      a caudal adjustable body slideably coupled to the caudal base body within the second recess and moveable within the perimeter of the second recess in a non-fixed position, wherein the caudal adjustable body slides within a caudal plane with respect to the caudal base body and wherein the caudal plane is parallel to the cranial plane; and
      a caudal articular surface coupled to the caudal adjustable body, wherein the cranial articular surface and the caudal articular surface are fashioned into complimentary shapes that moveably engage one another, and wherein the cranial articular surface and the caudal articular surface have a floating center of rotation with respect to at least one of the cranial base body and the caudal base body.

12. The total intervertebral disc replacement device of claim 11, further comprising:
   a first cranial actuator coupled to the cranial base body and engaging the cranial adjustable body, wherein the first cranial actuator controls sliding motion of the cranial adjustable body with respect to the cranial base body along a cranial AP axis;
   a second cranial actuator coupled to the cranial base body and engaging the cranial adjustable body, wherein the second cranial actuator controls sliding motion of the cranial adjustable body with respect to the cranial base body along a cranial lateral axis;
   a first caudal actuator coupled to the caudal base body and engaging the caudal adjustable body, wherein activation of the first caudal actuator controls sliding motion of the caudal adjustable body with respect to the caudal base body along a caudal AP axis; and
   a second caudal actuator coupled to the caudal base body and engaging the caudal adjustable body, wherein the second caudal actuator controls sliding motion of the caudal adjustable body with respect to the caudal base body along a caudal lateral axis.

13. The total intervertebral disc replacement device of claim 11, further comprising:
   an AP movement mechanism comprising:
      a first cranial track wherein a long axis of the cranial track is parallel to the cranial AP axis;
      a first cranial biasing member engaging the cranial adjustable body, wherein the cranial biasing member biases motion of the cranial adjustable body in a direction along the cranial AP axis relative to the cranial base body;
      a first caudal track wherein a long axis of the caudal track is parallel to the caudal AP axis; and
      a first caudal biasing member engaging the caudal adjustable body, wherein the first caudal biasing member biases motion of the caudal adjustable body in a direction along the caudal AP axis relative to the caudal base body; and
   a lateral movement mechanism comprising:
      a second cranial track wherein a long axis of the second cranial track is parallel to a cranial lateral axis;
      a second cranial biasing member engaging the cranial adjustable body, wherein the second cranial biasing member biases motion of the cranial adjustable body in a direction along the cranial lateral axis relative to the cranial base body; and
      a second caudal track wherein a long axis of the second caudal track is parallel to a caudal lateral axis; and
      a second caudal biasing member engaging the caudal adjustable body, wherein the second caudal biasing member biases motion of the caudal adjustable body in a direction along the caudal lateral axis relative to the caudal base body.

14. A method of surgically implanting a total intervertebral disc replacement device with a floating center of rotation, comprising the steps of:
   excising an intervertebral disc joint;
   coupling an intervertebral total disc replacement device to a vertebral body; and
   articulating a cranial articular surface with a caudal articular surface of a total intervertebral disc replacement device,
   wherein the articulation of the cranial articular surface and the caudal articular surface have a dynamic floating center of rotation which moves dynamically with respect to the vertebral body.

15. The method of claim 14, further comprising a step radiographing the position of the total intervertebral disc replacement device.

16. The method of claim 14, further comprising a step intraoperatively fluoroscoping the position of the total intervertebral disc replacement device.

17. The method of claim 14, further comprising a step adjusting the position of an articular surface of the coupled total intervertebral disc replacement device.

18. A total intervertebral disc replacement device comprising:
   a cranial member, comprising:
      a cranial base body,
      a cranial adjustable body coupled to the cranial base body and having a cranial articular surface;
   a caudal member, comprising:
      a caudal base body,
      a caudal adjustable body coupled to the caudal base body and having a caudal articular surface; and a joint comprising the cranial articular surface and the caudal articular surface, wherein the caudal articular surface moveably engages with the cranial articular surface, and wherein under a condition of the total intervertebral disc replacement device implanted between adjoining vertebral bodies in a spine, the joint is dynamically moveable with respect to at least one of the adjoining vertebral bodies in response to a force applied to at least one of the adjoining vertebral bodies.

19. The total intervertebral joint replacement device of claim 18, further comprising:
an actuator having
a stop and a biasing member,
wherein the actuator controls movement of an adjustable body and the biasing member biases the adjustable body against the actuator, and
wherein the adjustable body is coupled to at least one of a group comprised of the cranial member and the caudal member.

* * * * *